US008822650B2

(12) United States Patent
Jung et al.

(10) Patent No.: US 8,822,650 B2
(45) Date of Patent: *Sep. 2, 2014

(54) METHOD FOR THE MASS PRODUCTION OF IMMUNOGLOBULIN CONSTANT REGION

(75) Inventors: Sung Youb Jung, Suwon-si (KR); Jin Sun Kim, Gwangmyeong-si (KR); Young Jin Park, Suwon-si (KR); Ki-Doo Choi, Seoul (KR); Se Chang Kwon, Seoul (KR); Gwan Sun Lee, Seoul (KR)

(73) Assignee: Hanmi Science Co., Ltd, Hwaseong-si (KR)

( * ) Notice: Subject to any disclaimer, the term of this patent is extended or adjusted under 35 U.S.C. 154(b) by 198 days.

This patent is subject to a terminal disclaimer.

(21) Appl. No.: 13/087,593

(22) Filed: Apr. 15, 2011

(65) Prior Publication Data

US 2011/0245472 A1 Oct. 6, 2011

Related U.S. Application Data

(63) Continuation of application No. 10/535,312, filed as application No. PCT/KR2004/002943 on Nov. 13, 2004, now Pat. No. 8,029,789.

(30) Foreign Application Priority Data

Nov. 13, 2003 (KR) ........................ 10-2003-0080299

(51) Int. Cl.
*C12P 21/08* (2006.01)
*C07K 16/00* (2006.01)
*C07K 19/00* (2006.01)
*A61K 47/48* (2006.01)
*C07K 16/46* (2006.01)
*C07K 14/505* (2006.01)
*C07K 14/56* (2006.01)
*C07K 14/61* (2006.01)
*C07K 14/535* (2006.01)

(52) U.S. Cl.
CPC ........... *C07K 16/46* (2013.01); *C07K 2317/734* (2013.01); *C07K 19/00* (2013.01); *A61K 47/48507* (2013.01); *A61K 47/48423* (2013.01); *C07K 14/505* (2013.01); *C07K 14/56* (2013.01); *C07K 2319/30* (2013.01); *C07K 2317/732* (2013.01); *C07K 47/48415* (2013.01); *C07K 14/61* (2013.01); *C07K 14/535* (2013.01)
USPC ...................... 530/388.1; 435/69.6

(58) Field of Classification Search
USPC ...................... 530/388.1; 435/69.6
See application file for complete search history.

(56) References Cited

U.S. PATENT DOCUMENTS

| 5,045,312 A | 9/1991 | Aston et al. |
| 5,116,964 A | 5/1992 | Capon et al. |
| 5,349,053 A | 9/1994 | Landolfi |
| 5,585,097 A | 12/1996 | Bolt et al. |
| 5,605,690 A | 2/1997 | Jacobs et al. |
| 5,672,688 A | 9/1997 | Kobayashi et al. |
| 5,712,121 A | 1/1998 | Devos et al. |
| 5,723,125 A | 3/1998 | Chang et al. |
| 5,908,626 A | 6/1999 | Chang et al. |
| 6,030,613 A | 2/2000 | Blumberg et al. |
| 6,277,375 B1 | 8/2001 | Ward |
| 6,410,008 B1 | 6/2002 | Strom et al. |
| 6,444,792 B1 | 9/2002 | Gray et al. |
| 6,451,313 B1 | 9/2002 | Maddon et al. |
| 6,605,697 B1 | 8/2003 | Kwon et al. |
| 6,660,843 B1 | 12/2003 | Feige et al. |
| 6,797,493 B2 | 9/2004 | Sun et al. |
| 8,029,789 B2 * | 10/2011 | Jung et al. ................. 424/133.1 |
| 2001/0053539 A1 | 12/2001 | Lauffer et al. |
| 2002/0037558 A1 | 3/2002 | Lo et al. |
| 2002/0081664 A1 | 6/2002 | Lo et al. |
| 2003/0073164 A1 | 4/2003 | Simmons et al. |
| 2003/0082679 A1 | 5/2003 | Sun et al. |
| 2003/0082749 A1 | 5/2003 | Sun et al. |
| 2003/0104535 A1 | 6/2003 | Capon et al. |
| 2004/0044188 A1 | 3/2004 | Feige et al. |
| 2004/0053370 A1 | 3/2004 | Glaesner et al. |
| 2004/0053845 A1 | 3/2004 | Feige et al. |
| 2005/0048572 A1 | 3/2005 | Reilly et al. |

FOREIGN PATENT DOCUMENTS

| EP | 0 464 533 B1 | 1/1992 |
| EP | 0580171 A2 | 1/1994 |
| JP | 62-201582 | 9/1987 |
| JP | 2003-521925 A | 7/2003 |
| JP | 2004-537262 A | 12/2004 |
| JP | 2005-501052 A | 1/2005 |
| KR | 10-0249572 B1 | 12/1999 |

(Continued)

OTHER PUBLICATIONS

Andrews, B., et al., "A tightly regulated high level expression vector that utilizes a thermosensitive las repressor: production of the human T cell recepotr VB5.3 in *Escherichia coli*," Gene, 182:1-2, Dec. 5, 1996, pp. 101-109.

Kitai et al., "Extracellular Production of Human Immunoglobulin G Fc Region (hIgG-Fc) by *Escherichia coli*," Applied Microbiology Biotechnology, 1998, vol. 28, pp. 52-56.

(Continued)

*Primary Examiner* — Lynn Bristol
(74) *Attorney, Agent, or Firm* — Sughrue Mion, PLLC

(57) ABSTRACT

Disclosed are a recombinant expression vector comprising a nucleotide sequence encoding an *E. coli*-derived signal sequence and a nucleotide sequence encoding an immunoglobulin constant region, and a transformant transformed with the expression vector. Also, disclosed is a method of mass-producing an immunoglobulin constant region by culturing the transformant and expressing the immunoglobulin constant region in a water-soluble form.

10 Claims, 5 Drawing Sheets

(56) References Cited

FOREIGN PATENT DOCUMENTS

| KR | 10-0316347 | | 11/2001 |
|---|---|---|---|
| KR | 2003-0009464 | A | 1/2003 |
| WO | 97/24137 | A | 7/1997 |
| WO | 99/02709 | A | 1/1999 |
| WO | 00/15661 | | 3/2000 |
| WO | 00/23472 | A2 | 4/2000 |
| WO | 00/40615 | A2 | 7/2000 |
| WO | 00/69913 | A | 11/2000 |
| WO | 01/02440 | A1 | 1/2001 |
| WO | 01/03737 | | 1/2001 |
| WO | 01/03737 | A2 | 1/2001 |
| WO | 01/81415 | A2 | 11/2001 |
| WO | 01/83527 | A2 | 11/2001 |
| WO | 02/057435 | A2 | 7/2002 |
| WO | 03002144 | A1 | 1/2003 |
| WO | 03/074679 | | 6/2003 |
| WO | 03/077834 | A2 | 9/2003 |

OTHER PUBLICATIONS

Matsuda et al., "Proton Nuclear Magnetic Resonance Studies of the Structure of the Fc Fragment of Human Immunoglobulin Ga: Comparisons of Natice and Recombinant Proteins," Molecular Immunology, 1990, vol. 27, No. 6, pp. 571-579.

Japanese Office Action issued in corresponding JP Application No. 2006-539397, dated Sep. 22, 2010.

Stevenson et al., "Conjugation of Human Fcγ in Closed-Hinge or Open-Hinge Configuration to Fab'y and Analogous Ligands," The American Association of Immunologists, 1997, pp. 2242-2250.

Chapman et al., "PEGylated Antibodies and Antibody Fragments for Improved Therapy: A Review," Advanced Drug Delivery Reviews 54, 2002, pp. 531-545.

European Search Report issued in corresponding EP Application No. 10009129.7, dated Oct. 14, 2010.

Bentz et al., "Improved local delivery of TGF-P2 by binding to injectable fibrillar collagen via difunctional polyethylene glycol," J. Biomed. Mater. Res. 39(4):539-548 (Mar. 15, 1998).

Van Der Poll et al., "Effects of a recombinant dimeric tumor necrosis factor receptor on inflammatory responses to intravenous endotoxin in normal humans," Blood 89(10):3727-3734 (May 1997).

Simmons et al. (Nat. Biotech. 14:629-634 (1996)).

Sequence search alignment for SEQ ID No. 29 (p. 1; Nov. 30, 2009).
Sequence search alignment for SEQ ID No. 36 (p. 1; Dec. 1, 2009).
Sequence search alignment for SEQ ID No. 37 (pp. 1-2; Dec. 1, 2009).
Sequence search alignment for SEQ ID No. 38 (pp. 1-2; Dec. 1, 2009).
Sequence search alignment for SEQ ID No. 39 (pp. 1-2; Dec. 1, 2009).
Sequence search alignment for SEQ ID No. 40 (pp. 1-2; Dec. 1, 2009).
Sequence search alignment for SEQ ID No. 41 (pp. 1-2; Dec. 1, 2009).
Sequence search alignment for SEQ ID No. 42 (pp. 1-2; Dec. 1, 2009).
Sequence search alignment for SEQ ID No. 43 (pp. 1-2; Dec. 1, 2009).
Sequence search alignment for SEQ ID No. 44 (pp. 1-2; Dec. 1, 2009).
Sequence search alignment for SEQ ID No. 45 (pp. 1-2; Dec. 1, 2009).
Sequence search alignment for SEQ ID No: 46 (pp. 1-2; Dec. 1, 2009).

Wan et al. (Mol. Endocrinol. 17:2240-30 (2003)).
Bowie et al., (Science 247:1306 (1990)).
Lund et al. (The Journal of Immunology 1996, 157:4963-4969).
Adib-Conquy et al. (Protein Engineering 8:859-863 (1995).
Simmons and Yansura, Nature Biotechnol. 14:629-634, 1996.
Simmons et al., J. Immunol. Methods (2002) 263:133-147.
Sequence search alignment with the peptide sequence of SEQ ID No. 29.
Adib-Conquy et al., Protein Engineering 8:859-863 (1995) (Abstract).
Data sheet from Fermantas Life Sciences for "Bacterial alkaline phosphatase" derived from *E. coli* (pp. 1-3).

\* cited by examiner

METHOD FOR THE MASS PRODUCTION OF IMMUNOGLOBULIN CONSTANT REGION

CROSS-REFERENCE TO RELATED APPLICATIONS

This application is a continuation application of U.S. application Ser. No. 10/535,312 (now U.S. Pat. No. 8,029,789), filed Jun. 5, 2006, which is a §371 National Phase Entry Application of PCT/KR2004/002943, filed on Nov. 13, 2004, which claims the benefit of Korean Patent Application No. 10-2003-0080299, filed on Nov. 13, 2003 in the Korean Intellectual Property Office, the disclosures of which are incorporated herein in their entireties by reference.

TECHNICAL FIELD

The present invention relates to a recombinant expression vector comprising a nucleotide sequence encoding an *E. coli*-derived signal sequence and a nucleotide sequence encoding an immunoglobulin constant region, a transformant transformed with the expression vector, and a method of mass-producing an immunoglobulin constant region by culturing the transformant and expressing the immunoglobulin constant region in a water-soluble form.

BACKGROUND ART

With advances in genetic engineering, a large number of protein drugs have been prepared and utilized. However, protein drugs are susceptible to denaturator or proteolytic degradation in the body, and it is difficult to sustain in vivo concentrations and titers for a long period of time. Developing a technique to maintain the in vivo concentrations of protein drugs at suitable levels by enhancing protein stability is important to promote the efficacy of therapy, to help the patients who need to take their protein drug in frequent injections and to reduce the cost of treatment.

Many attempts have been made to enhance the in vivo stability of protein drugs for a long time, and such attempts include the changing a protein formulation, fusing a protein to another protein, or chemically or biologically attaching a suitable polymer to the surface of a protein.

One of such technique is making a fusion protein with the immunoglobulin Fc fragment.

The Fc fragment mediates effector functions such as complement-dependent cytotoxicity (CDC) or antibody-dependent cell-mediated cytotoxicity (ADCC), as well as antigen binding capacity that is the unique function of immunoglobulins. Also, the Fc fragment contains a sequence participating in the binding to the neonatal Fc receptor (FcRn), which plays a role in regulating serum IgG levels by increasing the transport of maternal IgG to neonates and the half-life of the IgG (Ghetie and Ward, *Immunology Today* 18: 592-598, 1997), and the sequence regulates the interaction between protein A and protein G. Through the fusion of this Fc fragment with a therapeutic protein, many studies have been performed to enhance the stability of the therapeutic protein.

For example, Korean Pat. No. 249572 discloses a fusion protein which is prepared by linking an IgG1 heavy chain constant region (Fc) at an amino terminal end thereof to a carboxyl terminal end of a protein, such as IL4 receptor, IL7 receptor, G-CSF receptor or EPO receptor, and producing the resulting fusion protein in mammalian cells. U.S. Pat. No. 5,605,690 describes a fusion protein comprising tumor necrosis factor receptor fused at its carboxyl terminal end to a human IgG1 Fc derivative, the fusion protein being produced in animal cells. Also, Tanox Inc. reported in U.S. Pat. Nos. 5,723,125 and 5,908,626 that a hybrid molecule comprises human interferon alpha or beta linked at its carboxyl terminal end to native human IgG4 Fc through a peptide linker and is produced in animal cells. Lexigen Inc., as described in International PCT Application Publication No. WO 00/69913, prepared a native IgG1 Fc linked at its carboxyl terminal end to the amino terminal end of human interferon by genetic recombination without the use of a linker and produced the fusion protein in animal cells. U.S. Pat. Publication No. 20030082679 discloses a fusion protein with an extended serum half-life, which comprises human G-CSF linked at its carboxyl terminal end to the amino terminal end of IgG1 Fc and is produced in animal cells. U.S. Pat. Publication No. 20010053539, U.S. Pat. No. 6,030,613, International PCT Application Publication Nos. WO 99/02709 and WO 01/03737 and European Pat. No. 0464533B1 disclose an Fc fusion protein with a longer serum half-life than a native protein, which comprises an IgG1 Fc or Fc derivative linked at its amino terminal end through a peptide linker or without a peptide linker to the carboxyl terminal end of human EPO, TPO, human growth hormone or human interferon beta, the Fc fusion protein being produced in animal cells.

These Fc fusion proteins, as described above, increase the serum half-life of a target protein, but are problematic in terms of mediating effector functions by the Fc fragment (U.S. Pat. No. 5,349,053). Through the effector functions of the Fc fragment, they fix complements or bind to cells expressing FcγRs, leading to lysis of specific cells, and induce the production and secretion of several cytokines inducing inflammation, leading to unwanted inflammation. Also, the fusion creates a new amino acid sequence at a connection region between the Fc fragment and the protein partner, which could potentially induce immune responses upon administration for a long time.

In this regard, many efforts have been made to prepare an immunoglobulin or immunoglobulin fragment having a long serum half-life but being deficient in effector functions. Cole et al. reported that, when amino acid residues of the CH2 region at positions 234, 235 and 237, known to play an important role in the binding to Fc receptors, are replaced with alanine to produce an Fc derivative having a reduced binding affinity to Fc receptors, the ADCC activity is inhibited (Cole et al., *J. Immunol.* 159: 3613-3621, 1997). However, in all of these variants, Fc may have increased immunogenicity or antigenicity compared to the native human Fc fragment due to the presence of unsuitable amino acids and may lose preferable Fc functions.

Among methods of deleting or reducing undesirable effector functions while maintaining high serum concentrations of an immunoglobulin, one is based on removing sugar moieties from the immunoglobulin. As described in U.S. Pat. No. 5,585,097, an aglycosylated antibody derivative as an anti-CD3 antibody can be prepared by replacing a glycosylated residue of antibodies, the asparagine residue at position 297 of the CH2 domain, with another amino acid. This aglycosylated antibody derivative exhibits reduced effector functions, but still retains its binding affinity to FcRn receptor with no change of serum half-life. However, this derivative is also problematic in terms of being potentially recognized as a foreign material and rejected by the immune system due to the production of a novel recombinant construct having an abnormal sequence. U.S. Pat. Publication No. 20030073164 discloses a method of producing an Fc derivative using *E. coli* devoid of glycosylation ability so as to prepare a therapeutic antibody deficient in effector functions.

The American company Amgen Inc. described, in U.S. Pat. No. 6,660,843 and U.S. Pat. Publication Nos. 20040044188 and 20040053845, a human IgG1 Fc derivative having amino acid deletions at the first five amino acid residues of the hinge region, which is fused to the amino or carboxyl terminal end of a therapeutic protein or a therapeutic protein mimicked by a peptide, and the production thereof using an *E. coli* host. However, this fusion protein not having a signal sequence is expressed as inclusion bodies and thus must be subjected to an additional refolding process. This protein refolding process reduces yields, and especially in a protein present as a homodimer or a heterodimer, remarkably reduces dimer production. Also, when a protein not having a signal sequence is expressed in *E. coli*, a methionine residue is added to the N-terminus of the expression product due to the feature of the protein expression system of *E. coli*. The aforementioned expression products of Amgen Inc. have an N-terminal methionine residue, which may induce immune responses upon repeated or excessive administration to the body. Also, since these fusion molecules are expressed in a fusion protein form in *E. coli* through linking a gene encoding a therapeutic protein to an Fc gene, they are difficult to express in *E. coli*, or a therapeutic protein is difficult to produce in *E. coli* if its expression in *E. coli* in a fused form results in a significant decrease or loss or activity. Further, since the fusion of two molecules creates a non-naturally occurring abnormal amino acid sequence at the connection region between two proteins, the fusion protein could be potentially recognized as "non-self" by the immune system and thus induce immune responses.

To solve these problems, the present inventors previously prepared an Fc fragment and a protein drug as separate polypeptides not using a fusion method based on genetic recombination but using the best expression systems and covalently linking the two polypeptides together to use the Fc fragment as a drug carrier. In this case, it is possible to prepare a conjugate of a glycosylated polypeptide drug and an aglycosylated Fc, which does not induce undesirable immune responses but has satisfactory properties of physiological drug activity, in vivo duration and stability.

In the above case, since it is preferable that the Fc is in an aglycosylated form, a prokaryotic expression system such as *E. coli* is used. Protein production methods using an *E. coli* expression system have several advantages compared to methods using animal cells, as follows. An *E. coli* expression vector can be easily constructed, thus allowing rapid evaluation for protein expression. Due to its rapid growth rate, *E. coli* allows mass production of a protein of interest at low cost. Also, a relatively simple expression process can be used. Thus, *E. coli* is more useful for commercial production than other host cells.

However, there is no report of an industrially available useful method for mass production in *E. coli* of immunoglobulin constant regions that are present as inclusion bodies upon overexpression in *E. coli*.

Thus, leading to the present invention, the intensive and through research into a method capable of mass-producing immunoglobulin constant regions such as an immunoglobulin Fc fragment, conducted by the present inventors, resulted in the finding that, when a nucleotide sequence encoding an immunoglobulin constant region such as an immunoglobulin Fc fragment is expressed in *E. coli* in a form fused to an *E. coli* signal sequence, the immunoglobulin constant region is expressed not as inclusion bodies but in a water-soluble form in *E. coli*.

DISCLOSURE OF THE INVENTION

It is therefore an object of the present invention to provide a method of mass-producing an immunoglobulin constant region, comprising transforming a prokaryotic cell with a recombinant expression vector including a nucleotide sequence encoding an *E. coli*-derived signal sequence and a nucleotide sequence encoding an immunoglobulin constant region; culturing a resulting transformant; and isolating and purifying the immunoglobulin constant region expressed in a water-soluble form by the transformant.

It is another object of the present invention to provide an immunoglobulin constant region prepared by the above method.

BRIEF DESCRIPTION OF THE DRAWINGS

The above and other objects, features and other advantages of the present invention will be more clearly understood from the following detailed description taken in conjunction with the accompanying drawings, in which:

In FIG. 1, lanes 1, 2 and 3 show products expressed in HM10927, HM10932 and HM10936, respectively, and lane 4 shows Fc generated by papain treatment of immunoglobulins produced in animal cells;

In FIG. 2, the A region shows proteins separated on a non-reduced SDS-PAGE gel, and the B region shows proteins on a reduced SDS-PAGE gel. Lane M indicates a prestained low-range standard protein marker (Bio-Rad), and lanes 1 to 4 of A and B regions indicate protein samples for immunoglobulin constant regions produced by *E. coli* transformants, HM10927, HM10928, HM10929 and HM10932 respectively;

In FIG. 3, the A region shows proteins separated on a non-reduced SDS-PAGE gel, and the B region shows proteins on a reduced SDS-PAGE gel. Lane M indicates the standard protein marker, and lanes 1 and 2 of A and B regions indicate protein samples for immunoglobulin constant regions produced by *E. coli* transformants, HM10930 and HM10934, respectively;

BEST MODE FOR CARRYING OUT THE INVENTION

Figure 1:
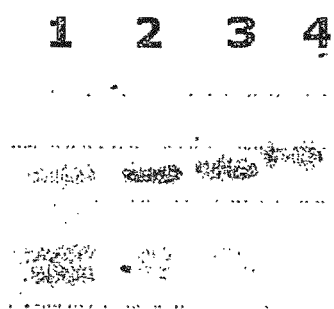
FIG. 1 shows the results of Western blotting of immunoglobulin Fc fragments expressed in *E. coli* transformants.

In one aspect, the present invention relates to a method of mass-producing an immunoglobulin constant region, comprising transforming a prokaryotic cell with a recombinant expression vector including a nucleotide sequence encoding an *E. coli*-derived signal sequence and a nucleotide sequence encoding an immunoglobulin constant region; culturing a resulting transformant; and isolating and purifying the immunoglobulin constant region expressed in a water-soluble form by the transformant.

Immunoglobulins are divided into variable regions that perform antibody functions of specifically binding to antigens and exhibit many variations on sequences, and constant regions that have fixed sequences and effector functions, including activating the complement system, conferring an ability to pass across the placenta and acting as ligands for receptors on various immune cells.

The present invention relates to a method of mass-producing an immunoglobulin constant region useful as a carrier for protein drugs. The immunoglobulin constant region capable of being produced by the present invention may be a native form isolated from humans and other animals including goats, swine, mice, rabbits, hamsters, rats and guinea pigs, or may be a recombinant or a derivative thereof, obtained from transformed animal cells or microorganisms. Preferred may be a constant region of IgG, IgA, IgM, IgE and IgD from humans, or a combination or hybrid thereof. The term "combination", as used herein, means that polypeptides encoding single-chain immunoglobulin Fc fragments of the same origin is linked to a single-chain polypeptide of a different origin to form a dimer or multimer. The term "hybrid", as used herein, means that sequences encoding two or more immunoglobulin Fc fragments of different origins are present in a single-chain immunoglobulin Fc fragment. The immunoglobulin may preferably be a constant region of IgG1, IgG2, IgG3 and IgG4, or a combination or hybrid thereof. In detail, there are five distinct types of heavy chains based on differences in the amino acid sequences of their constant regions: gamma ($\gamma$), mu ($\mu$), alpha ($\alpha$), delta ($\delta$) and epsilon ($\epsilon$), and the heavy chains include the following subclasses: gamma 1 ($\gamma$1), gamma 2 ($\gamma$2), gamma 3 ($\gamma$3), gamma 4 ($\gamma$4), alpha 1 ($\alpha$1) and alpha 2 ($\alpha$2). Also, there are two types of the light chains based on differences in the amino acid sequences of their constant regions: kappa ($\kappa$) and lambda ($\lambda$) types. Nucleotide sequences encoding human immunoglobulin constant regions and amino acid sequencing limiting the same, useful in the present invention, may be those encoded by nucleotide sequences from GenBank and/or EMBL database.

The heavy chain constant region of IgG, IgA, IgM, IgE consists of three domains: $C_H1$, $C_H2$ and $C_H3$, and the heavy chain of IgM further includes $C_H4$. The light chain has one constant domain, $C_L$. The immunoglobulin constant region of the present invention is one or more selected from the group consisting of $C_H1$, $C_H2$, $C_H3$, $C_H4$ and $C_L$ domains. The selected domain may be the whole or a fragment thereof (form having 30 or more amino acid deletions). For example, a CH1 domain, a CH2 domain, a CH3 domain and a CH4 domain; a CH1 domain and a CH2 domain; a CH1 domain and a CH3 domain; and a CH2 domain and a CH3 domain may be selected. However, the arrangement of the selected domains is not specifically limited.

The immunoglobulin constant region of the present invention includes an amino acid sequence derivative. The amino acid sequence derivative means to have a sequence in which one or more amino acid residues differ from a wild-type amino acid sequence, and may naturally occur or be artificially generated. The immunoglobulin constant region includes derivatives resulting from a deletion, an insertion, a non-conservative or conservative substitution or combinations thereof. An insertion is typically made by the addition of a consecutive amino acid sequence of about 1 to 20 amino acids, or may be made with a longer sequence. A deletion is typically in the range of about 1 to 30 amino acid residues. Amino acid exchanges in proteins and peptides, which do not generally alter the activity of the proteins, or peptides are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions.

Such derivatives may be prepared by a chemical peptide synthesis method or a DNA sequence-based recombinant method, which are known in the art (Sambrook et al., Molecular Cloning, Cold Spring Harbor Laboratory Press, New York, USA, 2d Ed., 1989).

In addition, the immunoglobulin constant region, if desired, may be modified by phosphorylation, sulfation, acrylation, glycosylation, methylation, farnesylation, acetylation, amidation, and the like.

The present invention may include a hinge region that allow a dimer formation. The hinge region may include, in addition to a native form, derivatives by a deletion, an insertion, a non-conservative or conservative substitution or combinations thereof.

The immunoglobulin derivative of the present invention is preferably a functional equivalent to its natural form having a similar biological activity, or, if desired, could be made by altering the property of the natural form. Preferably, the derivatives of the immunoglobulin constant region are proteins that have increased structural stability against heat, pH, etc., or solubility, or that have improved characteristics in terms of disulfide bond formation, compatibility with an expression host, complement binding, Fc receptor binding and antibody-dependent cell-mediated cytotoxicity (ADCC), so long as the derivatives produced do not induce unwanted immune responses in humans and animals. Preferred derivatives are as follows.

(1) A cysteine residue at a hinge region, responsible for disulfide bond formation, may be removed. Preferably, twelve residues among fifteen amino acids of the hinge region of IgG1, from the 1st amino acid, Glu, to the 12th amino acid, Pro, may be deleted to remove two cysteine residues. Also, nine residues among twelve amino acids of the hinge region of IgG4, from the 1st amino acid, Glu, to the 9th amino acid, Pro, may be deleted to remove one cysteine residue. This cysteine residue removal avoids the association with other proteins containing cysteine in host cells, thus improving expression levels and stability in a water-soluble form.

(2) An IgG1 constant region may be altered in a specific residue to have reduced affinity to Fc receptors mediating antibody-dependent cell-mediated cytotoxicity (ADCC). A derivative produced may contain a deletion or a replacement with another amino acid in the leucine residue at position 234 of an IgG1 CH2 sequence (see, the sequence from Kobat database for the numbering of the amino acid residues). Most preferably, Leu234 is replaced by phenylalanine, an amino acid residue at a corresponding position in IgG4. Such a derivative is not an unfamiliar sequence to humans, and thus is not expected to induce immune responses when administered to humans.

(3) A derivative of an IgG1 hinge region may contain a substitution at the first amino acid, proline. A proline residue, unlike other amino acid residues forms a closed ring structure. If proline is present at an amino terminal end, it may negatively affect the protein expression and elimination of a signal sequence. In this regard, the proline residue may be replaced by another amino acid, preferably serine, an amino acid residue at a corresponding position in IgG4. As noted above, this derivative is not an unfamiliar sequence to humans, and thus is not expected to induce immune responses when administered to humans.

The immunoglobulin constant region of the present invention includes a heavy chain constant region. Preferably, a heavy chain constant region containing a hinge region to allow the formation of an IgG1 dimer has the amino acid sequence of SEQ ID NO. 25, 21, 22 or 23. A heavy chain constant region not containing a hinge region to allow the formation of an IgG1 monomer has the amino acid sequence of SEQ ID NO. 27. Also, a heavy chain constant region containing a hinge region to allow the formation of an IgG2 dimer has the amino acid sequence of SEQ ID NO. 35. A heavy chain constant region containing a hinge region to allow the formation of an IgG4 dimer has the amino acid sequence of SEQ ID NO. 29 or 24. A heavy chain constant region not containing a hinge region to allow the formation of an IgG4 monomer has the amino acid sequence of SEQ ID NO. 30.

In addition, the immunoglobulin constant region of the present invention includes a light chain constant region. Preferably, the immunoglobulin light chain constant region has the amino acid sequence of SEQ ID NO. 34.

Further, the immunoglobulin constant region of the present invention includes both heavy chain and light chain constant regions. Preferred is a dimer or tetramer that contains a heavy chain constant region having the amino acid sequence of SEQ ID NO. 24 and a light chain constant region having the amino acid sequence of SEQ ID NO. 34.

When an immunoglobulin heavy chain region is overexpressed in a prokaryotic cell such as E. coli so as to be produced in an aglycosylated form, it is not completely folded and forms insoluble, inactive inclusion bodies by various mechanisms. Since inclusion bodies do not have activity as proteins, they need an additional denaturation and refolding process, which is conjugate and time-consuming, in order to be converted to a soluble form having biological activity. Thus, there is a need for the establishment of a mass production system useful in prokaryotic cells for the expression of an immunoglobulin heavy chain region as inclusion bodies.

E. coli proteins transported to the outside of the cytosol have an N-terminal sequence, which is typically cleaved off by a peptidase on the trans side of the membrane. By the sequence called "signal sequence" or "signal peptide", E. coli proteins are transported to the outside of the cytosol.

The term "signal sequence", as used herein, refers to a specific amino acid sequence that allows transport and secretion of a protein to the outside of the cytosol. The signal sequence of the present invention is an E. coli-derived signal sequence, which an E. coli secretory protein possesses. The E. coli-derived signal sequence is composed of 18 to 30 amino acids, and has several common features, as follows. The typical signal sequence possesses a very short amino-terminal N-domain of one to several positively charged amino acids, followed by a relatively long hydrophobic region, H-domain. At the amino terminal end, many polar positively charged amino acids, such as Lys and Arg, are present. The H-domain mainly contains hydrophobic residues such as Ala and Leu. A C-domain is located between the H-domain and a protein to be practically secreted, and has a sequence recognized by a signal peptidase. A protein having such a signal sequence arrives at the membrane by interaction with several proteins and is then cleaved at a specific site by a signal peptidase, releasing the mature protein. Non-limiting examples of the E. coli-derived signal sequence include alkaline phosphatase, penicillinase, Ipp, heat-stable enterotoxin II, LamB, PhoE, PelB, OmpA and maltose binding protein. The signal sequence of the present invention includes derivatives resulting from a deletion, an insertion, a non-conservative or conservative substitution or combinations thereof, so long as a protein expressed along with the signal sequence is allowed to be secreted to the outside of the cytosol. In particular, derivatives improving secretion efficacy of a fusion protein may be desirable.

The signal sequence is preferably heat-stable enterotoxin II. The heat-stable enterotoxin II includes its native form having the amino acid sequence of SEQ ID NO. 36 as well as derivatives thereof. It was previously reported that an E. coli heat-stable enterotoxin II signal sequence derivative improves the secretion efficiency of various heterogeneous proteins in E. coli (Korean Pat. Registration No. 0316347). An enterotoxin II derivative preferably has a replacement of an amino acid sequence of one or more amino acid residues at positions 2, 4, 5, 12, 20 and 22 by another amino acid sequence, and more preferably by the amino acid sequence of SEQ ID NO. 37, 38, 39, 40, 41, 42, 43, 44, 45 or 46. In the detailed practice of the present invention, an enterotoxin II having the amino acid sequence of SEQ ID NO. 38 was used, which is encoded by the nucleotide sequence of SEQ ID NO. 12.

A nucleic acid encoding the native enterotoxin II may be naturally isolated or synthesized by a gene synthesis method. An enterotoxin II derivative may be prepared by performing site-directed mutagenesis for a naturally isolated native form, or may be synthesized by a gene synthesis method.

The term "fusion protein", as used herein, means two or more different polypeptides that are linked through a peptide bond to become a single-chain polypeptide, and may be easily prepared by a genetic recombination method allowing translation into a single polypeptide. With the objects of the present invention, the fusion protein refers to comprise an immunoglobulin constant region fused to an E. coli-derived signal sequence. The signal sequence and the immunoglobulin constant region are in frame and translated into a single chain under the control of a single promoter, but the signal sequence is finally removed by cleavage from the translated polypeptide. A method of preparing the fusion protein is not specifically limited. Preferably, based on recombinant DNA technologies, the fusion protein is prepared by digesting a nucleic acid sequence encoding a signal sequence and another nucleic acid sequence encoding an immunoglobulin constant region with general restriction enzymes and ligating them with each other using an enzyme such as ligase.

A nucleic acid sequence encoding the fusion protein is expressed in the form of being inserted into a recombinant expression vector.

The term "recombinant expression vector", as used herein, which describes a vector capable of expressing a target protein in a suitable host cell, refers to a genetic construct that comprises essential regulatory elements to which a gene insert is operably linked in such a manner as to be expressed in a host cell.

The term "operably linked", as used herein, refers to a functional linkage between a nucleic acid expression control sequence and a second nucleic acid sequence coding for a target protein in such a manner as to allow general functions. The operable linkage to a recombinant vector may be prepared using a genetic recombinant technique well known in the art, and site-specific DNA cleavage and ligation may be carried out using enzymes generally known in the art.

A suitable expression vector includes expression regulatory elements, such as a promoter, an initiation codon, a stop codon, a polyadenylation signal and an enhancer. If E. coli is used as a host, the following promoters may be used: trp promoter, lac promoter, recA promoter, λP L promoter, lpp promoter and T7 promoter. If a host belongs to Bacillus sp., the following promoters may be used: SPO1 promoter, SPO2 promoter and penP promoter. However, the present invention is not limited to these examples.

The initiation and stop codons are necessary to be functional in an individual to whom a genetic construct has been administered, and must be in frame with the coding sequence. The promoter of the vector may be constitutive or inducible. In addition, expression vectors include a selectable marker that allows selection of host cells containing the vector, and replicable expression vectors include a replication origin.

The expression vector of the present invention is a vector essentially containing an E. coli signal sequence, and preferably containing an E. coli heat-stable enterotoxin II signal sequence. A vector, which includes an enterotoxin II Shine-Dalgarno (SD) sequence along with an enterotoxin II signal sequence, is more preferable because it further enhances expression levels of a target protein. In the present invention, to express an enterotoxin II signal sequence-immunoglobulin heavy chain region fusion protein, a nucleotide sequence encoding an enterotoxin II Shine-Dalgarno (SD) sequence and an enterotoxin II signal sequence is linked to another nucleotide sequence encoding an immunoglobulin heavy chain region by a genetic recombination method in such a way as to be expressed in frame under the control of a promoter.

In the detailed practice of the present invention, the following recombinant expression vectors are prepared: pSTIIG1CH1_3 expressing an immunoglobulin heavy chain region including an enterotoxin II signal sequence and the amino acid sequence of SEQ ID NO. 25; pSTIIdCG1Fc expressing an immunoglobulin heavy chain region including an enterotoxin II signal sequence and the amino acid sequence of SEQ ID NO. 21; pSTIIdCG1SFc expressing an immunoglobulin heavy chain region including an enterotoxin II signal sequence and the amino acid sequence of SEQ ID NO. 22; pSTIIdCG1SFFc expressing an immunoglobulin heavy chain region including an enterotoxin II signal sequence and the amino acid sequence of SEQ ID NO. 23; pSTIIG1Mo expressing an immunoglobulin heavy chain region including an enterotoxin II signal sequence and the amino acid sequence of SEQ ID NO. 27; pSTIIdCG2Fc expressing an immunoglobulin heavy chain region including an enterotoxin II signal sequence and the amino acid sequence of SEQ ID NO. 35; pSTIIdCG4Fc expressing an immunoglobulin heavy chain region including an enterotoxin II signal sequence and the amino acid sequence of SEQ ID NO. 29; pSTIIG4CH1_3 expressing an immunoglobulin heavy chain region including an enterotoxin II signal sequence and the amino acid sequence of SEQ ID NO. 24; and pSTIIG4Mo expressing an immunoglobulin heavy chain region including an enterotoxin II signal sequence and the amino acid sequence of SEQ ID NO. 30.

In the detailed practice of the present invention, a recombinant expression vector, pSTIIG4H_K, expresses an immunoglobulin heavy chain constant region including an enterotoxin II signal sequence and the amino acid sequence of SEQ ID NO. 24, and an immunoglobulin light chain region including an enterotoxin II signal sequence and the amino acid sequence of SEQ ID NO. 34, under the control of independent promoters.

The recombinant expression vectors expressing the fusion proteins are transformed into host cells.

With respect to the objects of the present invention, the host cells are prokaryotic cells where glycosylation does not occur. Examples of these prokaryotic cells include *Escherichia coli, Bacillus subtilis, Streptomyces, Pseudomonas, Proteus mirabilis* or *Staphylococcus*. Preferred is *E. coli*. Non-limiting examples of *E. coli* strains include BL21 (DE3), JM109, DH series, TOP10 and HB101, and the BL21 (DE3) strain is more preferable. When *E. coli* is used as a host cell, since *E. coli* does not have a system for protein glycosylation, an immunoglobulin constant region is produced in the form of being devoid of sugar moieties that are present in a CH2 domain of a native immunoglobulin. Sugar moieties of the immunoglobulin CH2 domain do not affect the structural stability of immunoglobulins, but cause immunoglobulins to mediate antibody-dependent cell-mediated cytotoxicity (ADCC) upon association with cells expressing Fc receptors and immune cells to secrete cytokines to induce inflammation. Also, the sugar moieties bind to the C1q part of the first complement component C1, leading to complement fixation. Thus, when an immunoglobulin constant region is produced in an aglycosylated form and linked to a therapeutic protein, the therapeutic protein is present in the serum for a prolonged period of time without the undesirable effector functions of immunoglobulins.

The transformation of the recombinant expression vectors into prokaryotic cells includes any methods by which nucleic acids can be introduced into cells, and, as known in the art, may be performed by selecting suitable standard techniques according to host cells. These methods include, but are not limited to, electroporation, protoplast fusion, calcium phosphate ($CaPO_4$) precipitation, calcium chloride ($CaCl_2$) precipitation, agitation with silicon carbide fiber, and PEG-, dextran sulfate- and lipofectamine-mediated transformation.

In the detailed practice of the present invention, the recombinant expression vectors are individually introduced into *E. coli*, thus generating the following transformants: BL21/pSTIIG1CH1_3(HM10935) transformed with pSTIIG1CH1_3; BL21/pSTIIdCG1Fc (HM10927) transformed with pSTIIdCG1Fc; BL21/pSTIIdCG1SFc (HM10928) transformed with pSTIIdCG1SFc; BL21/pSTIIdCG1SFFc (HM10929) transformed with pSTIIdCG1SFFc; BL21/pSTIIG1Mo (HM10930) transformed with pSTIIG1Mo; BL21/pSTIIdCG2Fc (HM10936) transformed with pSTIIdCG2Fc; BL21/pSTIIdCG4Fc (HM10932) transformed with pSTIIdCG4Fc; BL21/pSTIIG4CH1_3(HM10931) transformed with pSTIIG4CH1_3; BL21/pSTIIG4Mo(HM10933) transformed with pSTIIG4Mo; and BL21/pSTIIG4H_K (HM10934) transformed with pSTIIG4H_K.

The transformants transformed with the recombinant expression vectors are cultured by a general method. Culture conditions may be easily adjusted by those skilled in the art to be suitable for selected bacterial strains. Typically, a medium used in the culturing should contain all nutrients essential for the growth and survival of cells. The medium should contain a variety of carbon sources, nitrogen sources and trace elements. Examples of available carbon sources include glucose, sucrose, lactose, fructose, maltose, starch, carbohydrates such as cellulose, fats such as soybean oil, sunflower oil, castor oil and coconut oil, fatty acids such as palmitic acid, stearic acid and linoleic acid, alcohols such as glycerol and ethanol, and organic acids such as acetic acid. These carbon sources may be used singly or in combination of two or more. Examples of available nitrogen sources include organic nitrogen sources, such as peptone, yeast extract, meat extract, malt extract, corn steep liquor (CSL) and soybean whey, and inorganic nitrogen sources, such as urea, ammonium sulfate, ammonium chloride, ammonium phosphate, ammonium carbonate and ammonium nitrate. These nitrogen sources may be used singly or in combinations of two or more. A phosphorus source may be contained in the medium, which includes potassium dihydrogen phosphate, dipotassium hydrogen phosphate and corresponding sodium-containing salts. In addition, the medium may contain a metal salt, such as magnesium sulfate or iron sulfate. The medium may further include amino acids, vitamins, suitable precursors, and the like. The pH of the culture may be adjusted by adding a compound, such as ammonium hydroxide, potassium hydroxide, ammonia, phosphoric acid and sulfuric acid, to the culture by a suitable method. Also, during the culturing, antifoaming agents, such as polyglycol fatty acid esters, may be used to prevent bubble formation. To maintain the culture at favorable states, oxygen or an oxygen-containing gas (e.g., air) is introduced into the culture. The temperature of the culture is generally 20° C. to 45° C., and preferably 25° C. to 45° C.

After protein expression is confirmed in a small volume of the medium, large-scale expression may be carried out using a fermentor. Protein production using a fermentor should be carried out taking into consideration several factors, including the growth rate of host cells and protein expression levels.

Protein expression may be induced through adding, for example, IPTG to the medium under suitable culture conditions.

The immunoglobulin constant region fused to a signal sequence according to the present invention, expressed in a prokaryotic cell according to the above method, was surprisingly not expressed in the periplasmic space but was overexpressed in a water-soluble form in the cytoplasm, and the signal sequence was accurately processed. In the detailed practice of the present invention, the amount of the fusion protein secreted into the medium or periplasmic space was negligible. When cells were disrupted and subjected to Western blotting, proteins were overexpressed in the cytoplasm in a water-soluble form. Also, amino acid analysis of the N-terminal region of an immunoglobulin heavy chain region expressed in the cytoplasm revealed that a signal sequence is accurately processed.

This protein expression strategy is much more effective than conventional methods based on isolating active proteins from inclusion bodies as well as other conventional methods based on secreting target proteins into the periplasmic space or medium through fusion with various signal sequences. This is because the conventional methods have the following major disadvantages. First, the lipase protein aggregated by overexpression should undergo an additional complex process including dissolution and denaturation in a suitable solution and refolding using a refolding agent such as urea, guanidine or arginine (Kohno, Meth. Enzym. 185:187-195, 1990). Despite this complex process, the protein refolding efficiency is very low, and refolded proteins have lower activities than soluble proteins. Thus, this refolding method has no industrial benefits. Second, there are large differences between proteins to be expressed as recombinant forms in the degree of secretion into the periplasmic space or medium, aggregation degree after secretion, expression efficiency, and the like. As known previously, expression efficiencies are very low relative to proteins expressed in soluble forms in the cytoplasm. Also, proteins can be present as inclusion bodies even when secreted into the periplasmic space.

Thus, the present method provides a novel system useful for industrial mass production of immunoglobulin constant regions.

An immunoglobulin constant region overexpressed according to the present method may be purified by a general technique. The immunoglobulin constant regions of the present invention, produced by the transformants, may be isolated and purified by disrupting cells using a French press, an ultrasonicator, etc., and subjecting a water-soluble fraction containing the immunoglobulin constant region to, for example, salting out (e.g., ammonium sulfate precipitation, sodium phosphate precipitation, etc.), solvent precipitation (e.g., protein fraction precipitation using acetone, ethanol, etc.), dialysis, various chromatographies, such as gel filtration, ion exchange and reverse phase column chromatography, and ultrafiltration. These techniques are used singly or in combinations of two or more to obtain a protein coding for the immunoglobulin constant region of the present invention (Maniatis et al., Molecular Cloning: A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press (1989); Deutscher, M., Guide to Protein Purification Methods Enzymology, vol. 182. Academic Press. Inc., San Diego, Calif. (1990)).

In another aspect, the present invention relates to an immunoglobulin constant region prepared according to the above method.

The immunoglobulin constant region produced in prokaryotic cells such as *E. coli* according to the present method does not specifically have limited industrial applications. One exemplary application is use as a carrier for the formation of a conjugate with a certain drug. Construction of the conjugate comprising the immunoglobulin constant region linked to a drug is not specifically limited. For example, the immunoglobulin constant region and the drug may be linked together at various ratios, and the linkage may be mediated, for example, through a linker.

The drug includes polypeptides, compounds, extracts and nucleic acids. Preferred is a polypeptide drug (used with meaning identical to the word "protein"). The linker includes peptide and non-peptide linkers. Preferred is a non-peptide linker, and more preferred is a non-peptide polymer. A preferred example of the immunoglobulin heavy chain is Fc.

If the serum half-life needs to be enhanced, any physiologically active polypeptide may be used without specific limitation as a protein partner of the immunoglobulin constant region prepared according to the present method to form a conjugate. Such physiologically active polypeptides include those used for treating or preventing human diseases, which include cytokines, interleukins, interleukin binding protein, enzymes, antibodies, growth factors, transcription regulatory factors, coagulation factors, vaccines, structural proteins, ligand proteins or receptors, cell surface antigens, receptor antagonists, and derivatives and analogues thereof.

In detail, non-limiting examples of the physiologically active polypeptide include human growth hormone, growth hormone releasing hormone, growth hormone releasing peptide, interferons and interferon receptors (e.g., interferon-α, -β and -γ, water-soluble type I interferon receptor, etc.), colony stimulating factors, interleukins (e.g., interleukin-1, -2, -3, -4, -5, -6, -7, -8, -9, -10, -11, -12, -13, -14, -15, -16, -17, -18, -19, -20, -21, -22, -23, -24, -25, -26, -27, -28, -29, -30, etc.) and interleukin receptors (e.g., IL-1 receptor, IL-4 receptor, etc.), enzymes (e.g., glucocerebrosidase, iduronate-2-sulfatase, alpha-galactosidase-A, agalsidase alpha and beta, alpha-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin and cytokine binding proteins (e.g., IL-18 bp, TNF-binding protein, etc.), macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin, alpha-lactalbumin, apolipoprotein-E, erythropoietin, highly glycosylated erythropoietin, angiopoietins, hemoglobin, thrombin, thrombin receptor activating peptide, thrombomodulin, factor VII, factor VIIa, factor VIII, factor IX, factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors (e.g., nerve growth factor, ciliary neurotrophic factor, axogenesis factor-1, brain-natriuretic peptide, glial derived neurotrophic factor, netrin, neurophil inhibitor factor, neurotrophic factor, neuturin, etc.), parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors (e.g., TNFR(P75), TNFR (P55), IL-1 receptor, VEGF receptor, B cell activating factor receptor, etc.), receptor antagonists (e.g., IL1-Ra etc.), cell surface antigens (e.g., CD 2, 3, 4, 5, 7, 11a, 11b, 18, 19, 20, 23, 25, 33, 38, 40, 45, 69, etc.), monoclonal antibodies, polyclonal antibodies, antibody fragments (e.g., scFv, Fab, Fab', F(ab')2 and Fd), and virus derived vaccine antigens. The physiologically active polypeptide useful in the present invention may be a native form, may be produced by genetic recombination using prokaryotic cells such as E. coli or eukaryotic cells such as yeast cells, insect cells and animal cells, or may be a derivative having one or more amino acid mutations but having the biological activity identical to the native form.

In a preferred embodiment of the present invention, an immunoglobulin constant region fragment produced by the BL21/pSTIIdCG1SFFc (HM10929) transformant was linked to human erythropoietin (EPO) using a water-soluble polymer, polyethylene glycol, thus providing an EPO-PEG-immunoglobulin constant region protein conjugate. This protein conjugate was found to exhibit extended serum half-life compared to the native EPO and the second generation EPO having improved serum half-life, Aranesp (Amgen). Thus, the immunoglobulin constant region produced in a water-soluble form using an E. coli signal sequence according to the present invention, in the form of being linked to a physiologically active polypeptide, may be useful for enhancing the serum half-life and physiological activity of the physiologically active polypeptide with no risk of inducing immune responses.

A better understanding of the present invention may be obtained through the following examples which are set forth to illustrate, but are not to be construed as the limit of the present invention.

EXAMPLE 1

Construction of Human Immunoglobulin IgG1 Fc Constant Region Expression Vector

<1-1> Construction of Dimeric IgG1 Constant Region Expression Vector

To clone heavy chain and light chain constant regions including the CH1 domain and hinge region of IgG1, RT-PCR was carried out using RNA isolated from human blood cells as a template, as follows. First, total RNA was isolated from about 6 ml of blood using a Qiamp RNA blood kit (Qiagen), and gene amplification was performed using the total RNA as a template and a One-Step RT-PCR kit (Qiagen). To amplify a heavy chain gene, a pair of primers represented by SEQ ID Nos. 1 and 2 was used, and to amplify a gene encoding the constant region of a kappa light chain, another pair of primers represented by SEQ ID Nos. 3 and 4 was used. To facilitate gene cloning, a HindIII recognition site was introduced into 5' primers of SEQ ID Nos. 1 and 3, and a BamHI recognition site containing a stop codon into 3' primers of SEQ ID Nos. 2 and 4. The amplified heavy chain and light chain constant region products were digested with HindIII and BamHI, respectively, and inserted into a pBluscript SK (–) plasmid (Stratagen) treated with the same restriction enzyme, thus giving pBG1CH1-3 and pBK, respectively. DNA sequencing analysis revealed that two genes cloned into the cloning vector, IgG1 heavy chain CH1-hinge-CH2-CH3 gene and light chain constant region gene, have nucleotide sequences of SEQ ID Nos. 5 and 6, respectively.

To construct vectors expressing IgG1 constant regions, PCR was carried out using the plasmid as prepared above as a template to amplify genes encoding the following constant region fragments. A pair of primers represented by SEQ ID Nos. 7 and 2 was designed to amplify the CH1, hinge region, CH2 and CH3 of IgG1. An Fc fragment lacking cysteine residues not participating in disulfide bond formation in the hinge region was amplified using three primer pairs of SEQ ID Nos. 8 and 2, 9 and 2, and 10 and 2. A gene amplified using a primer pair of SEQ ID Nos. 7 and 2 and the pBG1CH1-3 plasmid as a template contained the CH1-hinge-CH2-CH3 of IgG1 and encoded a protein having the amino acid sequence represented by SEQ ID No. 25. SEQ ID No. 8 is a nucleotide sequence starting from the 13th residue, proline, of 15 amino acid residues of the hinge region (Glu Pro Lys Ser Cys Asp Lys Thr His Thr Cys Pro Pro Cys Pro; SEQ ID No. 26). A gene amplified using a primer pair of SEQ ID Nos. 8 and 2 and the pBG1CH1-3 plasmid as a template encoded a protein having an amino acid sequence (SEQ ID No. 21) that encodes an amino terminal end starting from the Pro-Cys-Pro sequence of the hinge region and CH2 and CH3 domains, among the whole IgG1 constant region. SEQ ID No. 9 was prepared by replacing the 13th proline residue of the hinge region with serine, and SEQ ID No. 10 was prepared by replacing the 13th proline residue of the hinge region with serine and the 4th leucine residue of the CH2 with phenylalanine. Thus, genes amplified using two primer pairs of SEQ ID Nos. 9 and 2; and 10 and 2 and the pBG1CH1-3 plasmid as a template may express dimeric proteins (SEQ ID Nos. 22 and 23) through disulfide bonds between cysteine residues of the hinge region in host cells.

To clone the amplified IgG1 constant region fragments into an expression vector containing an E. coli signal sequence, an expression vector pT14S1SH-4T20V22Q (Korean Pat. No. 38061), previously developed by the present inventors, was used as a starting vector. This expression vector contains an E. coli heat-stable enterotoxin signal sequence derivative having the nucleotide sequence represented by SEQ ID No. 12. To facilitate cloning, a StuI recognition site was inserted into an end of the E. coli heat-stable enterotoxin signal sequence derivative of the pT14S1SH-4T20V22Q plasmid through site-directed mutagenesis using a pair of primers represented by SEQ ID Nos. 13 and 14 to induce mutagenesis to introduce the StuI site at a nucleotide sequence coding for the last amino acid residue of the signal sequence. This insertion of the StuI site was identified to be successful by DNA sequencing. The resulting pT14S1SH-4T20V22Q plasmid containing a StuI site was designated as "pmSTII". The pmSTII plasmid was treated with StuI and BamHI and subjected to agarose gel electrophoresis, and a large fragment (4.7 kb) was purified, which contained the *E. coli* heat-stable enterotoxin signal sequence derivative. Then, the amplified genes were digested with BamHI and ligated with the linearized expression vector, thus providing pSTIIG1CH1_3 (PCR product obtained using the primers of SEQ ID Nos. 7 and 2), and pSTIIdCG1Fc (PCR product obtained using the primers of SEQ ID Nos. 8 and 2), pSTIIdCG1SFc (PCR product obtained using the primers of SEQ ID Nos. 9 and 2), and pSTIIdCG1SFFc (PCR product obtained using the primers of SEQ ID Nos. 10 and 2). The final expression vectors were transformed into *E. coli* BL21 (DE3), and the resulting transformants were designated as "BL21/pSTIIG1CH1_3(HM10935)", "BL21/pSTIIdCG1Fc (HM10927)", "BL21/pSTIIdCG1SFc (HM10928)" and "BL21/pSTIIdCG1SFFc (HM10929)". The transformants were deposited at the Korean Culture Center of Microorganisms (KCCM; Yurim B/D, Honje 1-dong, Sudaemum-gu, Seoul, Republic of Korea) on Sep. 15, 2004 and assigned accession numbers KCCM-10600, KCCM-10588, KCCM-10589 and KCCM-10594.

<1-2> Construction of Monomeric IgG1 Constant Region Expression Vector

To clone an IgG1 constant region to be expressed in a monomeric form, PCR was carried out using a pair of primers represented by SEQ ID Nos. 11 and 2 and the same template as in the above <1-1>.

The PCR product was cloned into an expression vector, pmSTII, according to the same procedure as in the above <1-1>, thus providing pSTIIG1Mo (PCR product obtained using the primers of SEQ ID NOS. 11 and 2). This expression vector was transformed into *E. coli* BL21 (DE3), and the resulting transformant was designated as "BL21/pSTIIG1Mo (HM10930)", which was deposited at the Korean Culture Center of Microorganisms (KCCM) on Sep. 15, 2004 and assigned accession number KCCM-10595. A protein expressed by the expression vector is expressed from the CH2 domain and presents in a monomeric form because it lacks the hinge region, and has the amino acid sequence of SEQ ID No. 27.

EXAMPLE 2

Construction of Human Immunoglobulin IgG2 Fc Expression Vector

To clone an IgG2 Fc gene, RT-PCR was carried out according to the same method as in the <1-1> of Example 1 using RNA isolated from human blood cells as a template and a One-Step RT-PCR kit (Qiagen). To obtain a desired gene sequence, a pair of primers represented by SEQ ID Nos. 31 and 32 was used. SEQ ID No. 31 is a nucleotide sequence starting from the 10th residue, proline, of 12 amino acid residues of the hinge region (Glu Arg Lys Cys Cys Val Glu Cys Pro Pro Cys Pro; SEQ ID NO. 33). The gene amplified using the pair of primers represented by SEQ ID Nos. 31 and 32 was identified to contain an amino terminal end starting with the Pro-Cys-Pro sequence of the hinge region and CH2 and CH3 domains, among a full-length IgG2 Fc gene sequence, and has the nucleotide sequence of SEQ ID No. 35. To clone the amplified IgG2 Fc gene into an expression vector containing an *E. coli* signal sequence, the aforementioned pmSTII vector was used. According to a cloning procedure similar to that in the <1-1> of Example 1, the pmSTII plasmid was treated with StuI and BamHI and subjected to agarose gel electrophoresis, and a large fragment (4.7 kb) was purified, which contained the *E. coli* heat-stable enterotoxin signal sequence derivative. Then, the amplified IgG2 Fc gene was digested with BamHI and ligated with the linearized expression vector, thus providing pSTIIdCG2Fc. This vector expresses in a host cell a protein that has the amino acid sequence of SEQ ID No. 35 and is present in a dimeric form by disulfide bonds between cysteine residues in the hinge region. The final expression vector was transformed into *E. coli* BL21 (DE3), and the resulting transformant was designated as "BL21/pSTIIdCG2Fc (HM10936)".

EXAMPLE 3

Construction of Human Immunoglobulin IgG4 Constant Region Expression Vector

<3-1> Construction of Dimeric IgG4 Constant Region Expression Vector

To clone a heavy chain constant region of human immunoglobulin IgG4, site-directed mutagenesis was carried out using the pBG1CH1-3 plasmid of the <1-1> of Example 1, containing an IgG1 heavy chain constant region, as a template, thus providing a pBG4CH1-3 plasmid carrying a gene encoding the CH1-Hinge-CH2-CH3 of IgG4. DNA sequencing analysis revealed that the mutated DNA sequence contains a substitution of an IgG4 constant region for the IgG1 constant region and has the nucleotide sequence of SEQ ID No. 15. PCR was carried out according to the same method as in Example 1 except for the use of different primers and the pBG4CH1-3 plasmid as a template. This PCR was carried out to remove cysteine residues not participating in disulfide bond formation from the 5'-end of an IgG4 constant region, using the pBG4CH1-3 plasmid as a template and a pair of primers represented by SEQ ID Nos. 16 and 17. SEQ ID No. 16 is a nucleotide sequence starting from the 10th residue, serine, of 12 amino acid residues of the IgG4 hinge region (Glu Ser Lys Tyr Gly Pro Pro Cys Pro Ser Cys Pro: SEQ ID No. 28). SEQ ID No. 17 has a BamHI recognition site containing a stop codon. A gene amplified using the above primer pair encoded an amino terminal end starting from the Ser-Cys-Pro sequence of the hinge region and CH2 and CH3 domains, among the whole IgG4 constant region. The amplified gene was treated with BamHI and inserted into a StuI/BamHI-digested pmSTII plasmid, thus providing pSTIIG4Fc. A protein expressed by this expression vector has the amino acid sequence of SEQ ID No. 29 and is present in a dimeric form through disulfide bonds between cysteine residues of the hinge region. Also, to construct an expression vector for a constant region (CH1-Hinge-CH2-CH3) containing a CH1 domain, PCR was carried out using the pBG4CH1-3 as a template and a pair of primers represented by SEQ ID Nos. 19 and 17, and the PCR product was cloned according to the same method as described above, thus providing pSTIIG4CH1_3. A protein expressed by this expression vector has the amino acid sequence of SEQ ID No. 24.

In addition, a vector expressing both heavy chain and light chain constant regions of an immunoglobulin was constructed as follows. First, a desired gene was amplified using the pBK plasmid prepared in the <1-1> of Example 1 as a template and a set of primers represented by SEQ ID Nos. 20 and 4, and cloned into a pmSTII vector containing an *E. coli* heat-stable enterotoxin II signal sequence derivative, thus generating a pSTIIK plasmid. The pSTIIK plasmid included a gene fragment comprising a kappa light chain constant region linked to an *E. coli* heat-stable enterotoxin II signal sequence derivative. The pSTIIK plasmid was digested with HindIII and SalI to obtain an about 1.2-kb gene fragment containing sequences required for protein expression, including a promoter and a signal sequence. The 1.2-kb gene fragment was inserted into an NruI site of the pSTIIG4CH1_3 vector, thus providing a pSTIIG4H_K vector. This expression vector expresses a heavy chain constant region and a light chain constant region under the control of different promoters, and the expressed products form a dimer or tetramer linked through free cysteine residues in each chain. The above expression vectors were individually transformed into *E. coli* BL21 (DE3), and the resulting transformants were designated as "BL21/pSTIIG4CH1_3(HM10931)", "BL21/pSTIIdCG4Fc (HM10932)" and "BL21/pSTIIG4H_K (HM10934)", and deposited at KCCM (accession numbers: KCCM-10596, KCCM-10597 and KCCM-10599).

<3-2>Construction of Monomeric IgG4 Constant Region Expression Vector

To clone an IgG4 constant region to be expressed as a monomer, an IgG4 CH2-3 gene was amplified using a pair of primers of SEQ ID Nos. 18 and 17 according to the same method as in the <3-1> of Example 3, and was cloned into an expression vector, pmSTII, thus providing a pSTIIG4Mo plasmid. This expression vector was transformed into *E. coli* BL21 (DE3), and the resulting transformant was designated as "BL21/pSTIIG4Mo (HM10933)", which was deposited at KCCM on Sep. 15, 2004 and assigned accession number KCCM-10598. A protein expressed by the expression vector has the amino acid sequence of SEQ ID No. 30, is expressed from the CH2 domain, and is present in a monomeric form because it lacks the hinge region.

The recombinant expression vectors, capable of expressing an immunoglobulin constant region in a water-soluble form in *E. coli* using an *E. coli* heat-stable enterotoxin II signal sequence derivative, and microorganisms transformed with the expression vectors are summarized in Table 1, below.

First, each transformant was grown in 100 ml of LB medium with agitation overnight and inoculated in the fermentor for large-scale culture. The fermentor was maintained at 30° C. or 35° C. To prevent conversion from an aerobic to an anaerobic environment, the cultures were aerated with 20-vvm air and stirred at 500 rpm. To compensate for the insufficient nutrients for bacterial growth during fermentation, the cultures were supplemented with glucose and yeast extracts according to the fermented states of bacteria. When the cultures reached an $OD_{600}$ value of 80, an inducer, IPTG, was added to the cultures to induce protein expression. The cultures were further cultured for 40 to 45 hrs until the OD value at 600 nm increased to 100 to 120.

The expression of immunoglobulin Fc in the *E. coli* transformants and the expressed sites, water solubility and dimer formation of the expressed Ig Fc were examined as follows. To determine whether an expressed product is secreted to the fermentation fluid or the periplasmic space of *E. coli* by the signal sequence fused to the expression vector, the fermentation fluid was centrifuged to obtain a cell-free fermentation fluid and collect cells. The cell-free fermentation fluid and a periplasmic space solution obtained by osmotic shock of the collected cells were subjected to Western blot analysis. As a result, a very small amount of immunoglobulin Fc was detected. To investigate intracellular expression of Ig Fc, cells were disrupted using an ultrasonicator (Misonix Company). The resulting cell lysate was centrifuged to separate water-soluble substances from water-insoluble substances, and the water-soluble substances were subjected to Western blot analysis, as follows. The water-soluble substances were mixed with a protein sample buffer not containing a reducing agent such as DTT or β-mercaptoethanol, and separated on a

TABLE 1

| Expression vectors | Transformants | Constitution of expressed proteins |
|---|---|---|
| pSTIIdCG1Fc | BL21/pSTIIdCG1Fc (HM10927) | G1 Fc (12 amino acid deletions at the Hinge region of SEQ ID No. 26) |
| pSTIIdCG1SFc | BL21/pSTIIdCG1SFc (HM10928) | G1 Fc (12 amino acid deletions at the Hinge region of SEQ ID No. 26 and a substitution of Ser for the first residue) |
| pSTIIdCG1SFFc | BL21/pSTIIdCG1SFFc (HM10929) | G1 Fc (12 amino acid deletions at the Hinge region of SEQ ID No. 26 and a substitution of Phe for the 234th Ser residue) |
| pSTIIG1Mo | BL21/pSTIIG1Mo (HM10930) | G1 Fc (15 amino acid deletions at the Hinge region of SEQ ID No. 26) |
| pSTIIdCG2Fc | BL21/pSTIIdCG2Fc (HM10936) | G2 Fc (9 amino acid deletions at the Hinge region of SEQ ID No. 33) |
| pSTIIG4CH1 3 | BL21/pSTIIG4CH1 3 (HM10931) | G4 CH1-hinge-CH2-CH3 |
| pSTIIdCG4Fc | BL21/pSTIIdCG4Fc (HM10932) | G4 Fc (9 amino acid deletions at the Hinge region of SEQ ID No. 28) |
| pSTIIG4Mo | BL21/pSTIIG4Mo (HM10933) | G4 Fc (12 amino acid deletions at the Hinge region of SEQ ID No. 28) |
| pSTIIG4H_K | BL21/pSTIIG4H_K (HM10934) | G4 CH1-hinge (SEQ ID No. 28)-CH2-CH3 and light chain constant region |
| pSTIIG1CH1_3 | BL21/pSTIIG1CH1_3 (HM10935) | G1 CH1-hinge (SEQ ID No. 26)-CH2-CH3 |

EXAMPLE 4

Expression and Purification of Immunoglobulin Constant Regions

<4-1> Expression and Purification

Bacterial transformants prepared in Examples 1, 2 were individually inoculated in a fermentor (Marubishi Company) and allowed to ferment, and were evaluated to determine whether they express immunoglobulin constant region fragments.

15% SDS-PAGE gel (Criterion Gel, Bio-Rad). Then, proteins were transferred onto a nitrocellulose membrane and detected with an HRP-conjugated anti-human Fc antibody (Sigma). As shown in FIG. 1, immunoglobulin Fc was overexpressed in a water-soluble form and located in the cytosol of *E. coli*. Also, products, expressed by transformants transformed with expression vectors expressing Ig Fc having a portion of a hinge region, were expressed as dimers. In FIG. 1, lanes 1, 2 and 3 show products expressed in HM10927, HM10932 and HM10936, respectively, and lane 4 shows Fc generated by papain treatment of immunoglobulins produced in animal cells, which showed a slightly larger size due to its sugar moieties on the SDS-PAGE gel than that produced in *E. coli*.

<4-2> N-Terminal Sequence Analysis

The water-soluble dimeric Ig Fc fragments, which were located in the cytosol of *E. coli* as demonstrated in the above <4-1>, were designed to be translated in a fused form to a signal sequence. Thus, to determine whether the Ig Fc fragments are located in *E. coli* cytosol in a form fused to the signal sequence when not secreted without signal sequence processing, N-terminal amino acid sequences of the Ig Fc fragments were determined by the Basic Science Research Institute, Seoul, Korea. Samples used in the N-terminal amino acid sequence analysis were prepared as follows.

First, a PVDF membrane (Bio-Rad) was immersed in methanol for about 2-3 sec to be activated, and was sufficiently wet with a blocking buffer (170 mM glycine, 25 mM Tris-HCl (pH 8.0), 20% methanol). The protein samples separated on a non-reduced SDS-PAGE gel, prepared in the above <4-1>, were blotted onto a PVDF membrane for about one hour using a blotting kit (Hoefer Semi-Dry Transfer unit, Amersham). Proteins transferred onto the PVDF membrane were stained with a protein dye, Coomassie Blue R-250 (Amnesco), for 3-4 sec, and washed with a destaining solution (water:acetic acid:methanol=5:1:4). Then, fragments containing proteins from the membrane were cut out with scissors and subjected to N-terminal sequence analysis.

As a result, the IgG 1 Fc protein was found to have an N-terminal sequence of Pro-Cys-Pro-Ala-Pro-Glu-Leu-Leu-Gly-Gly (SEQ ID NO: 47), the IgG4 Fc protein has an N-terminal sequence of Ser-Cys-Pro-Ala-Pro-Glu-Phe-Leu-Gly-Gly (SEQ ID NO: 48), and the IgG2 Fc protein has an N-terminal sequence of Pro-Cys-Pro-Ala-Pro-Pro-Val-Ala-Gly-Pro (SEQ ID NO: 49). As apparent from these results, the Fc fragments expressed by the *E. coli* transformants of the present invention were found to have an accurate N-terminal sequence. These results indicate that, when expressed in a form fused to a signal sequence, the Fc fragments are not secreted to the extracellular membrane or perplasmic space, are accurately processes in the signal sequence even upon overexpression and are present in a water-soluble form in the cytosol.

To determine the expression of immunoglobulin constant regions in the *E. coli* transformants, immunoglobulin constant regions were purified using a protein-A affinity column known to have strong affinity to immunoglobulin, as follows.

*E. coli* cells collected by centrifuging fermentation fluids were disrupted by a microfluizer (Microfludics) to give cell lysates. The cell lysates were subjected to two-step column chromatography to purify recombinant immunoglobulin constant regions present in the cytosol. 5 ml of a protein-A affinity column (Pharmacia) was equilibrated with PBS, and the cell lysates were loaded onto the column at a flow rate of 5 ml/min. Unbound proteins were washed out with PBS, and bound proteins were eluted with 100 mM citrate (pH 3.0). The collected fractions were desalted using a HiPrep 26/10 desalting column (Pharmacia) with 10 mM Tris buffer (pH 8.0). Then, secondary anion exchange column chromatography was carried out using 50 ml of a Q HP 26/10 column (Pharmacia). The primary purified recombinant immunoglobulin constant regions were loaded onto the Q-Sepharose HP 26/10 column, and the column was eluted with a linear gradient of 0-0.2 M NaCl in 10 mM Tris buffer (pH 8.0), thus providing highly pure fractions. After being partially purified using the protein-A affinity column, expression levels of the recombinant Ig constant regions were determined, and the results are given in Table 2, below.

TABLE 2

| Plasmids | Transformants | Expression levels (mg/L) measured after Protein-A purification |
|---|---|---|
| pSTIIdCG1Fc | HM10927 | 400 |
| pSTIIdCG1SFc | HM10928 | 100 |
| pSTIIdCG1SFFc | HM10929 | 600 |
| pSTIIG1Mo | HM10930 | 500 |
| pSTIIdCG2Fc | HM10936 | 100 |
| pSTIIG4CH1_3 | HM10931 | 80 |
| pSTIIdCG4Fc | HM10932 | 400 |
| pSTIIG4H_K | HM10934 | 50 |
| pSTIIG4Mo | HM10933 | 600 |
| pSTIIG1CH1_3 | HM10935 | 80 |

<4-3> Analysis of Expressed Proteins

Since the immunoglobulin constant regions thus obtained are present in a dimeric or monomeric form of the heavy chain, they have different migration patterns on reduced SDS-PAGE and non-reduced SDS-PAGE. The results of SDS-PAGE analysis, performed to determine protein purities after expressed products were purified, are given in FIGS. 2 and 3.

Figure 2:
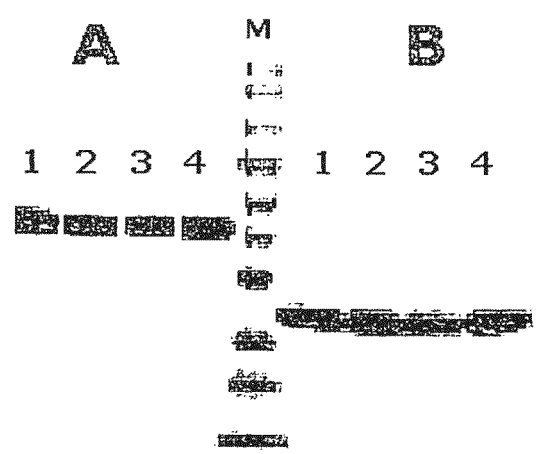
FIG. 2 shows the results of non-reduced and reduced SDS-PAGE of dimeric immunoglobulin Fc fragments expressed in *E. coli* transformants.
Figure 3:
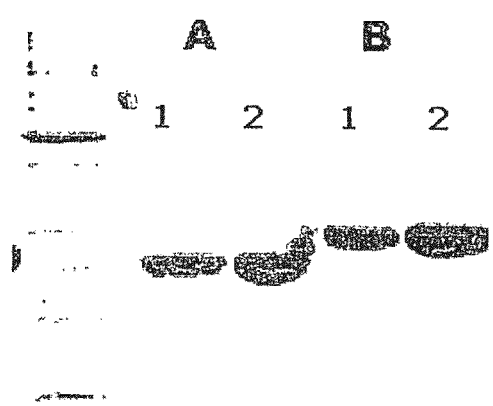
FIG. 3 shows the results of non-reduced and reduced SDS-PAGE of monomeric immunoglobulin Fc fragments expressed in *E. coli* transformants.

FIGS. 2 and 3 show the results of SDS-PAGE analysis of the purified immunoglobulin constant regions in a dimeric or monomeric form under non-reduced and reduced conditions using a criterion gel (Bio-Rad), wherein the constant regions were evaluated for differential migration on reduced versus non-reduced gels. In FIG. 2, the A region shows proteins separated on a non-reduced SDS-PAGE gel, and the B region shows proteins on a reduced SDS-PAGE gel. Lane M indicates a prestained low-range standard protein marker (Bio-Rad), and lanes 1 to 4 indicate protein samples for immunoglobulin constant regions produced by *E. coli* transformants, HM10927, HM10928, HM10929 and HM10932 respectively. As shown in FIG. 2, on reduced SDS-PAGE, the Ig Fc fragments were present in a monomeric form because disulfide bonds formed between cysteine residues of the hinge region were reduced, and were thus migrated the monomer distance. In contrast, on non-reduced SDS-PAGE, the Ig Fc fragments were present in a dimeric form by disulfide bonds and thus had a migration distance of about 42 kDa.

In FIG. 3, the A region shows proteins separated on a non-reduced SDS-PAGE gel, and the B region shows proteins on a reduced SDS-PAGE gel. Lane M indicates the standard protein marker, and lanes 1 and 2 indicate protein samples for immunoglobulin constant regions produced by *E. coli* transformants, HM10930 and HM10934, respectively. As shown in FIG. 2, the proteins did not show a large difference in migration on reduced versus non-reduced gels, and only displayed a slightly different migration due to the reduction of intramolecular disulfide bonds.

EXAMPLE 5

C1q Binding Assay-Using ELISA

To determine whether the derivatives prepared in Example 4 and proteins corresponding to the constant regions of immunoglobulins, expressed in the *E. coli* transformants and purified, bind to human C1q, an enzyme linked immunosorbent assay (ELISA) was carried out as follows. As test groups, immunoglobulin constant regions produced by the HM10929, HM10930, HM10932 and HM10933 transformants prepared in the above Examples were used. As standards, a glycosylated immunoglobulin (IVIGG-globulin S, Green Cross PBM) was used. The test and standard samples were prepared in 10 mM carbonate buffer (pH 9.6) at a concentration of 1 µg/ml. The samples were aliquoted into a 96-well plate (Nunc) in an amount of 200 ng per well, and the plate was coated overnight at 4° C. Then, each well was washed with PBS-T (137 mM NaCl, 2 mM KCl, 10 mM $Na_2HPO_4$, 2 mM $KH_2PO_4$, 0.05% Tween 20) three times, blocked with 250 µl of a blocking buffer (1% bovine serum albumin in PBS-T) at room temperature for 1 hr, and washed again with the same PBS-T three times. The standard and test samples were diluted in PBS-T to a predetermined concentration and added to antibody-coated wells, and the plate was incubated at room temperature for 1 hr and washed with PBS-T three times. Thereafter, 2 µg/ml C1q (R&D Systems) was added to the plate and reacted at room temperature for 2 hrs, and the plate was washed with PBS-T six times. 200 µl of a 1:1000 dilution of a human anti-human C1q antibody-peroxidase conjugate (Biogenesis, USA) in the blocking buffer was added to each well and reacted at room temperature for 1 hr. After each well was washed with PBS-T three times, equal volumes of color reagents A and B (Color A: stabilized peroxide and Color B: stabilized chromogen; DY 999, R&D Systems) were mixed, and 200 µl of the mixture was added to each well, followed by incubation for 30 min. Then, 50 µl of a reaction termination solution, 2 M sulphuric acid, was added to each well. The plate was read using a microplate reader (Molecular Device). Absorbance of standard and test samples was measured at 450 nm, and the results are given in FIG. 4, respectively.

Figure 4:
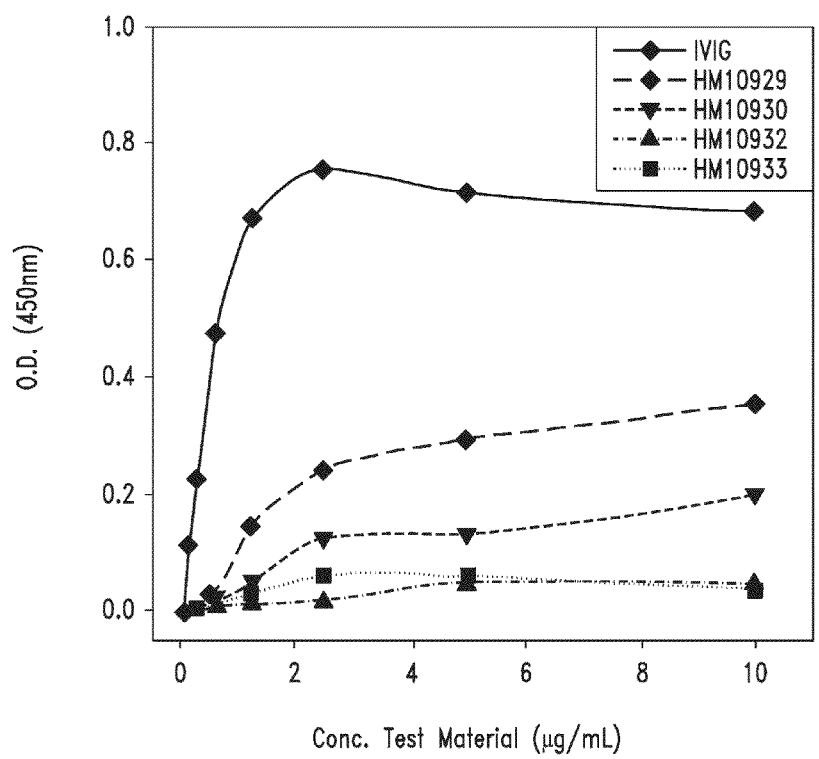
FIG. 4 shows the results of ELISA for the Clq binding capacity of immunoglobulin Fc fragments expressed in *E. coli* transformants and a native immunoglobulin.

As shown in FIG. 4, the immunoglobulin constant region proteins produced in *E. coli* according to the present invention exhibited markedly reduced binding affinity to C1q. These results indicate that the immunoglobulin constant region proteins of the present invention rarely have the risk of inducing immune responses such as cytotoxicity and inflammation in the body when used as a carrier for physiologically active polypeptides in a conjugate form.

EXAMPLE 6

Preparation and Pharmacokinetic Analysis of Human EPO Conjugate

<6-1> Preparation of Human EPO

To prepare a human EPO (erythropoietin) conjugate, first, an EPO gene was amplified by RT-PCR using total RNA isolated from blood cells and cloned into a pBluscript II (Stratagen) vector, thus generating a pBlueEP vector. To transfer the cloned EPO gene into an animal cell expression vector pCMV/dhfr-, the pBlueEP was digested with HindIII and BamHI, and an EPO gene-containing fragment was inserted into the animal cell expression vector treated with the same restriction enzymes, thus providing pcmvEP. This expression vector carrying an EPO gene was transfected into CHO cells allowing protein expression using a Lipofectamine reagent (Gibco). The cells were treated with MTX, and MTX concentrations gradually increased to 120 nM to elevate expression levels. EPO was expressed at high levels, higher than 100 mg per liter.

<6-2> Preparation of Human EPO-PEG Complex 3.4-kDa polyethylene glycol having an aldehyde reactive group at both ends, ALD-PEG-ALD (Shearwater), was mixed with the EPO prepared in the <6-1>, dissolved in 100 mM phosphate buffer in an amount of 5 mg/ml, at an EPO:PEG molar ratio of 1:1, 1:2.5, 1:5, 1:10 and 1:20. To this mixture, a reducing agent, sodium cyanoborohydride (NaCNBH$_3$, Sigma), was added at a final concentration of 20 mM and was allowed to react at 4° C. for 2 hrs with gentle agitation to allow PEG to link to the amino terminal end of EPO. To obtain a 1:1 complex of PEG and EPO, the reaction mixture was subjected to size exclusion chromatography using a Superdex® column (Pharmacia). The EPO-PEG complex was eluted from the column using 10 mM potassium phosphate buffer (pH 6.0) as an elution buffer, and EPO not linked to PEG, unreacted PEG and dimer byproducts where PEG was linked to two EPO molecules were removed. The purified EPO-PEG complex was concentrated to 5 mg/ml. Through this experiment, the optimal reaction molar ratio for EPO to PEG, providing the highest reactivity and generating the smallest amount of byproducts such as dimers, was found to be 1:2.5 to 1:5.

<6-3> Preparation of Conjugate of Human EPO-PEG Complex and Recombinant Immunoglobulin Constant Region The EPO-PEG complex prepared in the <6-2> was linked to an immunoglobulin constant region produced by the HM10929 in the <4-3> of Example 4. In detail, the immunoglobulin constant region fragment (about 53 kDa) prepared in the <4-3> was dissolved in 10 mM phosphate buffer and mixed with the EPO-PEG complex at an EPO-PEG complex: constant region molar ratio of 1:1, 1:2, 1:4 and 1:8. After the phosphate buffer concentration of the reaction solution was adjusted to 100 mM, a reducing agent, NaCNBH$_3$, was added to the reaction solution at a final concentration of 20 mM and was allowed to react at 4° C. for 20 hrs with gentle agitation. Through this experiment, the optimal reaction molar ratio for EPO-PEG complex to constant region fragment, providing the highest reactivity and generating the fewest byproducts such as dimers, was found to be 1:2.

After the coupling reaction, the reaction mixture was subjected to high-pressure liquid chromatography so as to eliminate unreacted substances and byproducts. The coupling reaction solution was desalted using a HiPrep 26/10 desalting column (Pharmacia) with 10 mM Tris buffer (pH 8.0). Then, the reaction solution was then loaded onto 50 ml of a Q HP 26/10 column (Pharmacia) at a flow rate of 8 ml/min, and this column was eluted with a linear NaCl gradient of 0-0.2 M to obtain desired fractions. The collected fractions were again loaded onto a polyCAT 21.5×250 column equilibrated with 10 mM acetate buffer (pH 5.2) at a flow rate of 15 ml/min, and this column was eluted with a linear NaCl gradient of 0.1-0.3 M, thus providing highly pure fractions.

<6-4> Pharmacokinetic Analysis

The native EPO prepared in the <5-1> of Example 5, Aranesp (Amgen) having greater sialic acid content to increase the half-life, and the EPO-PEG-Fc conjugate (test group) prepared in the <5-3> of Example 5 were subcutaneously injected at a dose of 100 µg/kg to five SD rats per group.

After the subcutaneous injection, blood samples were collected at 0.5, 1, 2, 4, 6, 12, 24 and 48 hrs in the control groups, and, in the test groups, at 1, 12, 24, 30, 48, 72, 96, 120, 144, 168, 192, 240, 288, 336 and 384 hrs. The blood samples were collected in 1.5 ml tubes, coagulated, and centrifuged for 10 min using an Eppendorf high-speed micro centrifugator to remove blood cells. Serum protein levels were measured by ELISA using an antibody specific to EPO.

Figure 5:
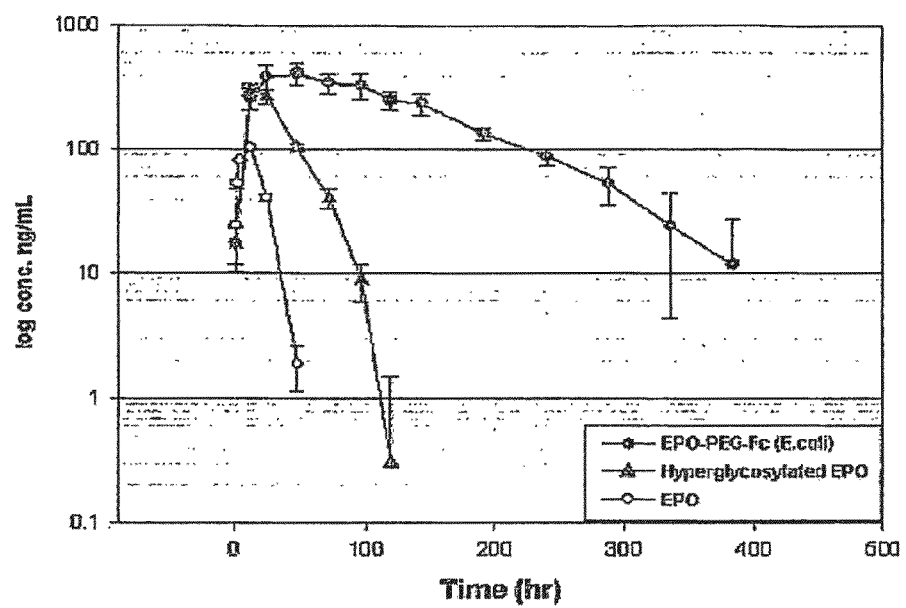
FIG. 5 is a graph showing the results of pharmacokinetic analysis of a native EPO, Aranesp and an EPO-PEG-*E. coli*-derived Fc conjugate. The native EPO prepared in the <5-1> of Example 5, Aranesp (Amgen) having greater silaic acid content to increase the half life, and the EPO-PEG-Fc conjugate (test group) prepared in the <5-3> of Example 5 were subcutaneously injected at a dose of 1004 kg to five SD rats per group.

Table 3, below, and FIG. 5 show serum half-lives of the native protein and the protein conjugate, respectively. The EPO-PEG-Fc (*E. coli*) protein conjugate, prepared using the immunoglobulin constant region produced according to the present invention as a carrier, exhibited a longer serum half-life than the native EPO. This extended half-life was found to be higher than that of Aranesp, a hyperglycosylated EPO having a long serum half-life.

TABLE 3

|  | EPO | EPO-PEG-Fc conjugate | Highly glycosylated EPO |
| --- | --- | --- | --- |
| $C_{max}^{1}$ (ng/ml) | 103.9 | 411.6 | 305.0 |
| $T_{max}^{2}$ (hr) | 12.0 | 48.0 | 12.0 |
| $T_{1/2}^{3}$ (hr) | 6.1 | 66.7 | 11.6 |

TABLE 3-continued

| | EPO | EPO-PEG-Fc conjugate | Highly glycosylated EPO |
|---|---|---|---|
| AUC[4] (ng·hr/ml) | 2310.5 | 65203 | 12117 |
| MRT[5] (hr) | 14.5 | 118.2 | 30.3 |

[1]Maximal serum concentration
[2]Time taken to reach the maximal drug concentration
[3]Serum half-life of a drug
[4]Area under the serum concentration versus time curve
[5]Mean time that a drug molecule resides in the body

INDUSTRIAL APPLICABILITY

As described hereinbefore, the present method allows mass production of an immunoglobulin constant region in a water-soluble form using an *E. coli* signal sequence. The produced immunoglobulin constant region is useful when linked to a physiologically active protein for enhancing the serum half-life and physiological activity of the physiologically active protein with no risk of inducing immune responses.

The invention claimed is:

1. A method of producing an immunoglobulin constant region, comprising:
   (a) transforming an *E. coli* cell with a recombinant expression vector comprising (i) a nucleotide sequence encoding *E. coli* heat-stable enterotoxin II signal sequence and (ii) a nucleotide sequence encoding the immunoglobulin constant region without a variable region;
   (b) culturing a resulting *E. coli* transformant in a medium; and
   (c) isolating the immunoglobulin constant region expressed by the transformant, wherein the *E. coli* heat-stable enterotoxin II signal sequence is cleaved by a signal peptidase, and consists of the amino acid sequence of SEQ ID NO. 36, 37, 38, 39, 40, 41, 42, 43, 44, 45 or 46,
   wherein the immunoglobulin constant region is expressed in the cytoplasm in a water soluble form and is not secreted into the medium or the periplasmic space.

2. The method according to claim 1, wherein the immunoglobulin constant region is selected from the group consisting of constant regions from IgG, IgA, IgM, IgE, and IgD.

3. The method according to claim 2, wherein the IgG is selected from the group consisting of constant regions from IgG1, IgG2, IgG3, and IgG4.

4. The method according to claim 3, wherein the immunoglobulin constant region is an IgG4 constant region.

5. The method according to claim 4, wherein the immunoglobulin constant region is a human aglycosylated IgG4 constant region.

6. The method according to claim 1, wherein the immunoglobulin constant region is composed of one to three domains selected from the group consisting of CH1, CH2, CH3, and CH4 domains.

7. The method according to claim 6, wherein the immunoglobulin constant region further comprises a hinge region.

8. The method according to claim 1, wherein the recombinant expression vector comprises a nucleotide sequence encoding a heavy chain constant region and a nucleotide sequence encoding a light chain constant region.

9. The method according to claim 1, wherein the immunoglobulin constant region has an amino acid sequence represented by SEQ ID NO. 21, 22, 23, 24, 25, 27, 29, 30, 34 or 35.

10. The method according to claim 1, wherein the *E. coli* transformant is *E. coli* BL21/pSTIIG1CH1_3 (HM10935) of Accession No. KCCM-10600, BL21/pSTIIdCG1Fc (HM10927) of Accession No. KCCM-10588, BL21/pSTIIdCG1SFc (HM10928) of Accession No. KCCM-10589, BL21/pSTIIdCG1SFFc (HM10929) of Accession No. KCCM-10594, BL21/pSTIIG1Mo (HM10930) of Accession No. KCCM-10595, BL21/pSTIIdCG4Fc (HM10932) of Accession No. KCCM-10597, BL21/pSTIIG4-CH1_3 (HM10931) of Accession No. KCCM-10596, BL21/pSTIIG4Mo (HM10933) of Accession No. KCCM-10598, or BL21/pSTIIG4H_K (HM10934) of Accession No. KCCM-10599.

\* \* \* \* \*

SEQUENCE LISTING

<160> NUMBER OF SEQ ID NOS: 49

<210> SEQ ID NO 1
<211> LENGTH: 37
<212> TYPE: DNA
<213> ORGANISM: Artificial Sequence
<220> FEATURE:
<223> OTHER INFORMATION: primer

<400> SEQUENCE: 1
cccaagcttg cctccaccaa gggcccatcg gtcttcc                    37

<210> SEQ ID NO 2
<211> LENGTH: 33
<212> TYPE: DNA
<213> ORGANISM: Artificial Sequence
<220> FEATURE:
<223> OTHER INFORMATION: primer

<400> SEQUENCE: 2
gggggatcct catttacccg gagacaggga gag                        33

<210> SEQ ID NO 3
<211> LENGTH: 35
<212> TYPE: DNA
<213> ORGANISM: Artificial Sequence
<220> FEATURE:
<223> OTHER INFORMATION: primer

<400> SEQUENCE: 3
cccaagcttg acatccagtt gacccagtct ccatc                      35

<210> SEQ ID NO 4
<211> LENGTH: 36
<212> TYPE: DNA
<213> ORGANISM: Artificial Sequence
<220> FEATURE:
<223> OTHER INFORMATION: primer

<400> SEQUENCE: 4
gggggatcct caacactctc ccctgttgaa gctctt                     36

<210> SEQ ID NO 5
<211> LENGTH: 990
<212> TYPE: DNA
<213> ORGANISM: Homo sapiens

<400> SEQUENCE: 5
gcctccacca agggcccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180

```
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agagccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                    990
```

```
<210> SEQ ID NO 6
<211> LENGTH: 324
<212> TYPE: DNA
<213> ORGANISM: Homo sapiens

<400> SEQUENCE: 6
cgaactgtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg ttag                                           324
```

```
<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
cggcctccac caagggccca tcggtcttcc                                      30
```

```
<210> SEQ ID NO 8
<211> LENGTH: 33
<212> TYPE: DNA
<213> ORGANISM: Artificial Sequence
<220> FEATURE:
<223> OTHER INFORMATION: primer

<400> SEQUENCE: 8
cgccgtgccc agcacctgaa ctcctggggg gac                                  33
```

```
<210> SEQ ID NO 9
<211> LENGTH: 33
<212> TYPE: DNA
<213> ORGANISM: Artificial Sequence
<220> FEATURE:
```

<223> OTHER INFORMATION: primer

<400> SEQUENCE: 9
cgtcatgccc agcacctgaa ctcctggggg gac                            33

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10
cgtcatgccc agcacctgag ttcctggggg gacca                          35

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
cggcacctga actcctgggg ggaccg                                    26

<210> SEQ ID NO 12
<211> LENGTH: 69
<212> TYPE: DNA
<213> ORGANISM: Escherichia coli

<400> SEQUENCE: 12
atgaaaaaga caatcgcatt tcttcttgca tctatgttcg tttttttctat tgctacaaat    60 gcccaggcg                                                              69

<210> SEQ ID NO 13
<211> LENGTH: 45
<212> TYPE: DNA
<213> ORGANISM: Artificial Sequence
<220> FEATURE:
<223> OTHER INFORMATION: primer

<400> SEQUENCE: 13
tctattgcta caaatgccca ggccttccca accattccct tatcc                45

<210> SEQ ID NO 14
<211> LENGTH: 45
<212> TYPE: DNA
<213> ORGANISM: Artificial Sequence
<220> FEATURE:
<223> OTHER INFORMATION: primer

<400> SEQUENCE: 14
agataacgat gtttacgggt ccggaagggt tggtaaggga atagg                45

<210> SEQ ID NO 15
<211> LENGTH: 984
<212> TYPE: DNA
<213> ORGANISM: Homo sapiens

<400> SEQUENCE: 15
gcttccacca agggcccatc cgtcttcccc ctggcgccct gctccaggag cacctccgag    60
agcacagccg ccctgggctg cctggtcaag gactacttcc ccgaaccggt gacggtgtcg   120
tggaactcag gcgccctgac cagcggcgtg cacaccttcc cggctgtcct acagtcctca   180

```
ggactctact ccctcagcag cgtggtgacc gtgccctcca gcagcttggg cacgaagacc    240
tacacctgca acgtagatca caagcccagc aacaccaagg tggacaagag agttgagtcc    300
aaatatggtc ccccatgccc atcatgccca gcacctgagt tcctgggggg accatcagtc    360
ttcctgttcc ccccaaaacc caaggacact ctcatgatct cccggacccc tgaggtcacg    420
tgcgtggtgg tggacgtgag ccaggaagac cccgaggtcc agttcaactg gtacgtggat    480
ggcgtggagg tgcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtcc tccatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggctcct tcttcctcta cagcaggcta accgtggaca agagcaggtg gcaggagggg    900
aatgtcttct catgctccgt gatgcatgag gctctgcaca accactacac acagaagagc    960
ctctccctgt ctctgggtaa atga                                          984

<210> SEQ ID NO 16
<211> LENGTH: 35
<212> TYPE: DNA
<213> ORGANISM: Artificial Sequence
<220> FEATURE:
<223> OTHER INFORMATION: primer

<400> SEQUENCE: 16
cgtcatgccc agcacctgag ttcctggggg gacca                              35

<210> SEQ ID NO 17
<211> LENGTH: 42
<212> TYPE: DNA
<213> ORGANISM: Artificial Sequence
<220> FEATURE:
<223> OTHER INFORMATION: primer

<400> SEQUENCE: 17
gggggatcct catttaccca gagacaggga gaggctcttc tg                      42

<210> SEQ ID NO 18
<211> LENGTH: 29
<212> TYPE: DNA
<213> ORGANISM: Artificial Sequence
<220> FEATURE:
<223> OTHER INFORMATION: primer

<400> SEQUENCE: 18
cggcacctga gttcctgggg ggaccatca                                     29

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
cggcttccac caagggccca tccgtcttcc                                    30

<210> SEQ ID NO 20
```

<211> LENGTH: 21
<212> TYPE: DNA
<213> ORGANISM: Artificial Sequence
<220> FEATURE:
<223> OTHER INFORMATION: primer

<400> SEQUENCE: 20
cgcgaactgt ggctgcacca t                                              21

<210> SEQ ID NO 21
<211> LENGTH: 220
<212> TYPE: PRT
<213> ORGANISM: Homo sapiens

<400> SEQUENCE: 21

Pro Cys Pro Ala Pro Glu Leu Leu Gly Gly Pro Ser Val Phe Leu Phe
 1               5                  10                  15

Pro Pro Lys Pro Lys Asp Thr Leu Met Ile Ser Arg Thr Pro Glu Val
             20                  25                  30

Thr Cys Val Val Val Asp Val Ser His Glu Asp Pro Glu Val Lys Phe
         35                  40                  45

Asn Trp Tyr Val Asp Gly Val Glu Val His Asn Ala Lys Thr Lys Pro
     50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 22
<211> LENGTH: 220
<212> TYPE: PRT
<213> ORGANISM: Homo sapiens

<400> SEQUENCE: 22

Ser Cys Pro Ala Pro Glu Leu Leu Gly Gly Pro Ser Val Phe Leu Phe
 1               5                  10                  15

Pro Pro Lys Pro Lys Asp Thr Leu Met Ile Ser Arg Thr Pro Glu Val
             20                  25                  30

Thr Cys Val Val Val Asp Val Ser His Glu Asp Pro Glu Val Lys Phe
         35                  40                  45

Asn Trp Tyr Val Asp Gly Val Glu Val His Asn Ala Lys Thr Lys Pro
     50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Ser Asn Gly Gln Pro
145                 150                 155                 160

Glu Asn Asn Tyr Lys Thr Thr Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 23
<211> LENGTH: 220
<212> TYPE: PRT
<213> ORGANISM: Homo sapiens

<400> SEQUENCE: 23

Ser Cys Pro Ala Pro Glu Phe Leu Gly Gly Pro Ser Val Phe Leu Phe
 1               5                  10                  15

Pro Pro Lys Pro Lys Asp Thr Leu Met Ile Ser Arg Thr Pro Glu Val
                 20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Ser Asn Gly Gln Pro
145                 150                 155                 160

Glu Asn Asn Tyr Lys Thr Thr Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys

-continued

```
                210                 215                 220

<210> SEQ ID NO 24
<211> LENGTH: 327
<212> TYPE: PRT
<213> ORGANISM: Homo sapiens

<400> SEQUENCE: 24

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 25
<211> LENGTH: 330
<212> TYPE: PRT
<213> ORGANISM: Homo sapiens
```

```
<400> SEQUENCE: 25

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 15
<212> TYPE: PRT
<213> ORGANISM: Homo sapiens

<400> SEQUENCE: 26

Glu Pro Lys Ser Cys Asp Lys Thr His Thr Cys Pro Pro Cys Pro
  1               5                  10                  15

<210> SEQ ID NO 27
<211> LENGTH: 217
```

<212> TYPE: PRT
<213> ORGANISM: Homo sapiens

<400> SEQUENCE: 27

```
Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 28
<211> LENGTH: 12
<212> TYPE: PRT
<213> ORGANISM: Homo sapiens

<400> SEQUENCE: 28

```
Glu Ser Lys Tyr Gly Pro Pro Cys Pro Ser Cys Pro
 1               5                  10
```

<210> SEQ ID NO 29
<211> LENGTH: 220
<212> TYPE: PRT
<213> ORGANISM: Homo sapiens

<400> SEQUENCE: 29

```
Ser Cys Pro Ala Pro Glu Phe Leu Gly Gly Pro Ser Val Phe Leu Phe
 1               5                  10                  15

Pro Pro Lys Pro Lys Asp Thr Leu Met Ile Ser Arg Thr Pro Glu Val
            20                  25                  30

Thr Cys Val Val Val Asp Val Ser Gln Glu Asp Pro Glu Val Gln Phe
        35                  40                  45

Asn Trp Tyr Val Asp Gly Val Glu Val His Asn Ala Lys Thr Lys Pro
    50                  55                  60

Arg Glu Glu Gln Phe Asn Ser Thr Tyr Arg Val Val Ser Val Leu Thr
```

```
                65                  70                  75                  80
Val Leu His Gln Asp Trp Leu Asn Gly Lys Glu Tyr Lys Cys Lys Val
                    85                  90                  95

Ser Asn Lys Gly Leu Pro Ser Ser Ile Glu Lys Thr Ile Ser Lys Ala
                100                 105                 110

Lys Gly Gln Pro Arg Glu Pro Gln Val Tyr Thr Leu Pro Pro Ser Gln
                115                 120                 125

Glu Glu Met Thr Lys Asn Gln Val Ser Leu Thr Cys Leu Val Lys Gly
                130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Arg Leu Thr Val Asp Lys Ser Arg Trp Gln Glu
                180                 185                 190

Gly Asn Val Phe Ser Cys Ser Val Met His Glu Ala Leu His Asn His
                195                 200                 205

Tyr Thr Gln Lys Ser Leu Ser Leu Ser Leu Gly Lys
                210                 215                 220

<210> SEQ ID NO 30
<211> LENGTH: 217
<212> TYPE: PRT
<213> ORGANISM: Homo sapiens

<400> SEQUENCE: 30

Ala Pro Glu Phe Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser Gln Glu Asp Pro Glu Val Gln Phe Asn Trp Tyr
                35                  40                  45

Val Asp Gly Val Glu Val His Asn Ala Lys Thr Lys Pro Arg Glu Glu
                50                  55                  60

Gln Phe Asn Ser Thr Tyr Arg Val Val Ser Val Leu Thr Val Leu His
 65                 70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
                100                 105                 110

Pro Arg Glu Pro Gln Val Tyr Thr Leu Pro Pro Ser Gln Glu Glu Met
                115                 120                 125

Thr Lys Asn Gln Val Ser Leu Thr Cys Leu Val Lys Gly Phe Tyr Pro
                130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
                180                 185                 190

Phe Ser Cys Ser Val Met His Glu Ala Leu His Asn His Tyr Thr Gln
                195                 200                 205

Lys Ser Leu Ser Leu Ser Leu Gly Lys
                210                 215
```

-continued

<210> SEQ ID NO 31
<211> LENGTH: 29
<212> TYPE: DNA
<213> ORGANISM: primer

<400> SEQUENCE: 31
cgccgtgccc agcacctccg gtggcggga                                    29

<210> SEQ ID NO 32
<211> LENGTH: 33
<212> TYPE: DNA
<213> ORGANISM: primer

<400> SEQUENCE: 32
gggggatcct catttacccg gagacaggga gag                               33

<210> SEQ ID NO 33
<211> LENGTH: 12
<212> TYPE: PRT
<213> ORGANISM: Homo sapiens

<400> SEQUENCE: 33

Glu Arg Lys Cys Cys Val Glu Cys Pro Pro Cys Pro
1               5                   10

<210> SEQ ID NO 34
<211> LENGTH: 107
<212> TYPE: PRT
<213> ORGANISM: Homo sapiens

<400> SEQUENCE: 34

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 35
<211> LENGTH: 219
<212> TYPE: PRT
<213> ORGANISM: Homo sapiens

<400> SEQUENCE: 35

Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

```
Glu Gln Phe Asn Ser Thr Phe Arg Val Val Ser Val Leu Thr Val
 65                  70                  75                  80

Val His Gln Asp Trp Leu Asn Gly Lys Glu Tyr Lys Cys Lys Val Ser
                 85                  90                  95

Asn Lys Gly Leu Pro Ala Pro Ile Glu Lys Thr Ile Ser Lys Thr Lys
            100                 105                 110

Gly Gln Pro Arg Glu Pro Gln Val Tyr Thr Leu Pro Pro Ser Arg Glu
        115                 120                 125

Glu Met Thr Lys Asn Gln Val Ser Leu Thr Cys Leu Val Lys Gly Phe
130                 135                 140

Tyr Pro Ser Asp Ile Ala Val Glu Trp Glu Ser Asn Gly Gln Pro Glu
145                 150                 155                 160

Asn Asn Tyr Lys Thr Thr Pro Pro Met Leu Asp Ser Asp Gly Ser Phe
                165                 170                 175

Phe Leu Tyr Ser Lys Leu Thr Val Asp Lys Ser Arg Trp Gln Gln Gly
            180                 185                 190

Asn Val Phe Ser Cys Ser Val Met His Glu Ala Leu His Asn His Tyr
        195                 200                 205

Thr Gln Lys Ser Leu Ser Leu Ser Pro Gly Lys
    210                 215

<210> SEQ ID NO 36
<211> LENGTH: 23
<212> TYPE: PRT
<213> ORGANISM: Escherichia coli

<400> SEQUENCE: 36

Met Lys Lys Asn Ile Ala Phe Leu Leu Ala Ser Met Phe Val Phe Ser
  1               5                  10                  15

Ile Ala Thr Asn Ala Tyr Ala
            20

<210> SEQ ID NO 37
<211> LENGTH: 23
<212> TYPE: PRT
<213> ORGANISM: Escherichia coli

<400> SEQUENCE: 37

Met Lys Lys Thr Ile Ala Phe Leu Leu Ala Ser Met Phe Val Phe Ser
  1               5                  10                  15

Ile Ala Thr Asn Ala Gln Ala
            20

<210> SEQ ID NO 38
<211> LENGTH: 23
<212> TYPE: PRT
<213> ORGANISM: Escherichia coli

<400> SEQUENCE: 38

Met Lys Lys Thr Ile Ala Phe Leu Leu Ala Ser Met Phe Val Phe Ser
  1               5                  10                  15

Ile Ala Thr Val Ala Gln Ala
            20

<210> SEQ ID NO 39
<211> LENGTH: 23
<212> TYPE: PRT
<213> ORGANISM: Escherichia coli
```

-continued

```
<400> SEQUENCE: 39

Met Lys Lys Thr Ala Phe Leu Leu Ala Ser Met Phe Val Phe Ser
1               5                   10                  15

Ile Ala Thr Asn Ala Gln Ala
            20

<210> SEQ ID NO 40
<211> LENGTH: 23
<212> TYPE: PRT
<213> ORGANISM: Escherichia coli

<400> SEQUENCE: 40

Met Lys Lys Ser Ile Ala Phe Leu Leu Ala Ser Met Phe Val Phe Ser
1               5                   10                  15

Ile Ala Thr Asn Ala Gln Ala
            20

<210> SEQ ID NO 41
<211> LENGTH: 23
<212> TYPE: PRT
<213> ORGANISM: Escherichia coli

<400> SEQUENCE: 41

Met Lys Lys Ser Ile Ala Phe Leu Leu Ala Ser Met Phe Val Phe Ser
1               5                   10                  15

Ile Ala Thr Val Ala Gln Ala
            20

<210> SEQ ID NO 42
<211> LENGTH: 23
<212> TYPE: PRT
<213> ORGANISM: Escherichia coli

<400> SEQUENCE: 42

Met Lys Lys Thr Ile Ala Phe Leu Leu Ala Ser Gly Phe Val Phe Ser
1               5                   10                  15

Ile Ala Thr Val Ala Gln Ala
            20

<210> SEQ ID NO 43
<211> LENGTH: 23
<212> TYPE: PRT
<213> ORGANISM: Escherichia coli

<400> SEQUENCE: 43

Met Lys Lys Thr Ile Ala Phe Leu Leu Ala Ser Leu Phe Val Phe Ser
1               5                   10                  15

Ile Ala Thr Val Ala Gln Ala
            20

<210> SEQ ID NO 44
<211> LENGTH: 23
<212> TYPE: PRT
<213> ORGANISM: Escherichia coli

<400> SEQUENCE: 44

Met Lys Lys Lys Ser Ala Phe Leu Leu Ala Ser Met Phe Val Phe Ser
1               5                   10                  15

Ile Ala Thr Asn Ala Gln Ala
            20
```

```
<210> SEQ ID NO 45
<211> LENGTH: 23
<212> TYPE: PRT
<213> ORGANISM: Escherichia coli

<400> SEQUENCE: 45

Met Val Lys Lys Thr Ala Phe Leu Leu Ala Ser Met Phe Val Phe Ser
1               5                   10                  15

Ile Ala Thr Asn Ala Gln Ala
            20

<210> SEQ ID NO 46
<211> LENGTH: 23
<212> TYPE: PRT
<213> ORGANISM: Escherichia coli

<400> SEQUENCE: 46

Met Lys Lys Lys Ile Ala Phe Leu Leu Ala Ser Met Phe Val Phe Ser
1               5                   10                  15

Ile Ala Thr Val Ala Gln Ala
            20

<210> SEQ ID NO 47
<211> LENGTH: 10
<212> TYPE: PRT
<213> ORGANISM: Homo sapiens

<400> SEQUENCE: 47

Pro Cys Pro Ala Pro Glu Leu Leu Gly Gly
1               5                   10

<210> SEQ ID NO 48
<211> LENGTH: 10
<212> TYPE: PRT
<213> ORGANISM: Homo sapiens

<400> SEQUENCE: 48

Ser Cys Pro Ala Pro Glu Phe Leu Gly Gly
1               5                   10

<210> SEQ ID NO 49
<211> LENGTH: 10
<212> TYPE: PRT
<213> ORGANISM: Homo sapiens

<400> SEQUENCE: 49

Pro Cys Pro Ala Pro Pro Val Ala Gly Pro
1               5                   10
```